United States Patent
Gascoyne et al.

(10) Patent No.: US 6,703,819 B2
(45) Date of Patent: Mar. 9, 2004

(54) PARTICLE IMPEDANCE SENSOR

(75) Inventors: Peter Gascoyne, Bellaire, TX (US); Tom Anderson, Houston, TX (US); Jody Vykoukal, Houston, TX (US); Frederick Becker, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/005,373

(22) Filed: Dec. 3, 2001

(65) Prior Publication Data

US 2003/0102854 A1 Jun. 5, 2003

(51) Int. Cl.[7] .............................................. G01N 27/00
(52) U.S. Cl. ........................................................ 324/71.4
(58) Field of Search .............................. 324/71.4, 71.1, 324/713, 691, 698, 715; 73/865.5, 866; 204/450, 547; 209/12.2, 127.1, 128, 212

(56) References Cited

U.S. PATENT DOCUMENTS

| 4,940,976 A | * | 7/1990 | Gastouniotis et al. | 340/870.02 |
| 5,454,472 A | | 10/1995 | Benecke et al. | 209/127.1 |
| 5,569,367 A | | 10/1996 | Betts et al. | 204/547 |

(List continued on next page.)

FOREIGN PATENT DOCUMENTS

| EP | 0513064 | 11/1992 |
| EP | 0625267 | 11/1994 |
| EP | 0680380 | 11/1995 |
| EP | 0691891 | 1/1996 |
| EP | 0898493 | 3/1999 |
| WO | WO 93/16383 | 8/1993 |
| WO | WO 94/16821 | 8/1994 |
| WO | WO 97/34689 | 9/1997 |
| WO | WO 98/04355 | 2/1998 |
| WO | WO 99/62622 | 12/1999 |
| WO | WO 00/69565 | 11/2000 |

OTHER PUBLICATIONS

"Bangor biochip heads for California," EPSRC Home Page: http://www.epsrc.ac.uk/documents/about$_{13}$ epsrc/corporate_publi ../bangor.ht, article printed on Dec. 26, 2000.
"Diagnostic dielectrophoresis–on–a–chip," *Science/Technology*, 77(8):32, 1999. Article printed from http://www-.pubs.acs.org/hotartcl/cenear/99022/7708scitobox.2.html on Dec. 26, 2000.
Allsopp et al., "Impedance technique for measuring dielectrophoretic collection of microbiological particles," *J. Phys. D: Appl. Phys.*, 32:1066–1074, 1999.
Balachandran et al., "Electrostatic atomization of conducting liquids using AC superimposed on DC fields," *IEEE Transactions on Industry Applications*, 30(4):850–854, 1994.

(List continued on next page.)

*Primary Examiner*—N. Le
(74) *Attorney, Agent, or Firm*—Fulbright & Jaworski, LLP

(57) ABSTRACT

Apparatuses and methods for analyzing particles using an impedance sensor. A flow-through impedance sensor may use two in-line electrodes driven in counter phase. A common sensor electrode may be used to, for example, detect impedance and determine trajectories through the sensor area. The sensor may be used in a wide variety of applications, including but not limited to use with microfluidic devices for determining particle characteristics such as position, velocity, size, and concentration as well as detection of bacterial spores and other biological agents of potential use in warfare and bio-terrorism.

40 Claims, 37 Drawing Sheets

U.S. PATENT DOCUMENTS

| | | | |
|---|---|---|---|
| 5,569,591 A | 10/1996 | Kell et al. | 435/29 |
| 5,571,401 A | 11/1996 | Lewis et al. | 205/787 |
| 5,580,435 A | 12/1996 | Kovacs | 204/603 |
| 5,653,859 A | 8/1997 | Parton et al. | 204/450 |
| 5,680,708 A * | 10/1997 | James | 33/366.12 |
| 5,683,569 A | 11/1997 | Chung et al. | 205/775 |
| 5,694,343 A * | 12/1997 | Nobutoki | 364/578 |
| 5,814,200 A | 9/1998 | Pethig et al. | 204/547 |
| 5,858,192 A | 1/1999 | Becker et al. | 204/547 |
| 5,888,370 A | 3/1999 | Becker et al. | 204/547 |
| 5,965,452 A | 10/1999 | Kovacs | 436/149 |
| 5,993,630 A | 11/1999 | Becker et al. | 204/547 |
| 5,993,631 A | 11/1999 | Parton et al. | 204/347 |
| 5,993,632 A | 11/1999 | Becker et al. | 204/547 |
| 6,010,616 A | 1/2000 | Lewis et al. | 205/787 |
| 6,017,696 A | 1/2000 | Heller | 435/6 |
| 6,084,503 A | 7/2000 | Ruile et al. | 340/10.1 |
| 6,093,308 A | 7/2000 | Lewis et al. | 205/787 |
| 6,099,803 A | 8/2000 | Ackley et al. | 422/68.1 |
| 6,113,768 A | 9/2000 | Fuhr et al. | 204/643 |
| 6,129,828 A | 10/2000 | Sheldon, III et al. | 204/518 |
| 6,149,789 A | 11/2000 | Benecke et al. | 204/547 |
| 6,169,394 B1 | 1/2001 | Frazier et al. | 324/71.4 |
| 6,224,745 B1 | 5/2001 | Baltruschat | 205/775 |
| 6,225,059 B1 | 5/2001 | Ackley et al. | 435/6 |
| 6,287,832 B1 | 9/2001 | Becker et al. | 435/173.9 |
| 6,294,063 B1 | 9/2001 | Becker et al. | 204/450 |
| 6,426,615 B1 * | 7/2002 | Mehta | 324/71.4 |
| 6,437,551 B1 * | 8/2002 | Krulevitch et al. | 324/7.1 |
| 6,466,021 B1 * | 10/2002 | MacEnany | 324/350 |

OTHER PUBLICATIONS

Cheng et al., "Preparation and hybridization analysis of DNA/RNA form *E. coli* on microfabricated bioelectronic chips," *Nature Biotechnology*, 16:541–546, 1998.

El–Kishky and Gorur, "Electric field and energy computation on wet insulating surfaces," *IEEE Transaction on Dielectrics and Electrical Insulation*, 3(4):587–593, 1996.

El–Kishky and Gorur, "Electric field computation on an insulating surface with discrete water droplets," *IEEE Transactions on Dielectrics and Electrical Insulation*, 3(3):450–456, 1996.

Fuller et al., "Microfabricated multi–frequency particle impedance characterization system," *Micro Total Analysis System*, van den Berg et al. (eds.), 265–268, 2000.

Galicki et al., "Electrohydrodynamic atomization of dielectric fluids," *Conference on Electrical Insulation and Dielectric Phenomena*, IEEE Annual Report, 365–368, 1996.

Gawad et al., "Impedance spectroscopy cell analysis in microchannels," *Micro Total Analysis Systems*, 253–255, 2001.

Gawad et al., "Micronarcined impedance spectroscopy flow cytometer for cell analysis and particle sizing," *Lab on a Chip*, 1:76–82, 2001.

He et al., "Droplet charge–to–mass ratio measurement in an EHD liquid–liquid extraction system," *IEEE Transactions on Industry Applications*, 32(1):146–154, 1996.

Higashiyama et al., "Behavior of water droplets located on a hydrophobic insulating plate under DC field," *IEEE*, 1808–1813, 1998.

Hoffman and Britt, "Flow–system measurement of a cell impedance properties," *J. Histochemistry and Cytochemistry*, 27:234–240, 1979.

Hoffman et al., "Flow cytometric electronic direct current volume and radiofrequency impedance measurements of single cells and particles," *Cytometry*, 1:377–384, 1981.

Hosokawa et al., "Handling of picoliter liquid samples in a Poly(dimethylsiloxane)–based microfluidic device," *Anal. Chem.*, 71:4781–4785, 1999.

Huneiti et al., "Harmonic Spraying of conducting liquids employing AC–DC electric fields," *IEEE Transactions on Industry Applications*, 34(2):279–285, 1998.

Jones, Electromechanics of Particles, Cambridge University Press, Cambridge, Chapter 3:34–82, 1995.

Kashyap and Gratzl, "Electrochemistry in microscopic domains. 1. The electrochemical cell and its voltammetric and amperometric response," *Anal. Chem.*, 70:1468–1476, 1998.

Kloes and Koenig, "Basic investigation of the performance of droplets on electrically stressed polymer surfaces," *Conference on Electrical Insulation and Dielectric Phenomena*, IEEE Annual Report, 374–377, 1997.

Lee and Kim, "Liquid micromotor driven by continuous electrowetting," *IEEE*, 538–543, 1998.

Metwally, "Electrostatic charging and modeling of aqueous sprays and fission of droplets," *Conference on Electrical Insulation and Dielectric Phenomena*, IEEE Annual Report, 117–120, 1996.

Mizuno et al., "Behavior of water droplets on silicone rubber sheet under AC voltage application," *IEEE*, 96–99, 1998.

Moesner et al., "Electrostatic devices for particle microhandling," *IEEE Transactions on Industry Applications*, 35(3):530–536, 1999.

Sathuvalli and Bayazitoglu, "The lorentz forces on an electrically conducting sphere in an alternating magnetic field," *IEEE Transactions on Magnetics*, 32(2):386–399, 1996.

Sato et al., "Experimental investigation of droplet formation mechanisms by electrostatic dispersion in a liquid–liquid system," *IEEE Transactions on Industry Applications*, 33(6):1527–1534, 1997.

Sato et al., "Production of oil/water type uniformly sized droplets using a convergent AC elctric field," *IEEE Transactions on Industry Applications*, 32(1):138–145, 1996.

Wang et al., "A theoretical method of electrical field analysis for dielectrophoretic electrode arrays using Green's theorum," *J. Phys. D: Appl. Phys.*, 29:1649–1660, 1996.

Wang et al., "Separation of polystyrene microbeads using dielectrophoretic/gravitational field–flow–fractionation," *Biophysical Journal*, 74:2689–2701, 1998.

Washizu, "Electrostatic actuation of liquid droplets for microreactor applications," *IEEE Transactions on Industry Applications*, 34(4):732–737, 1998.

* cited by examiner

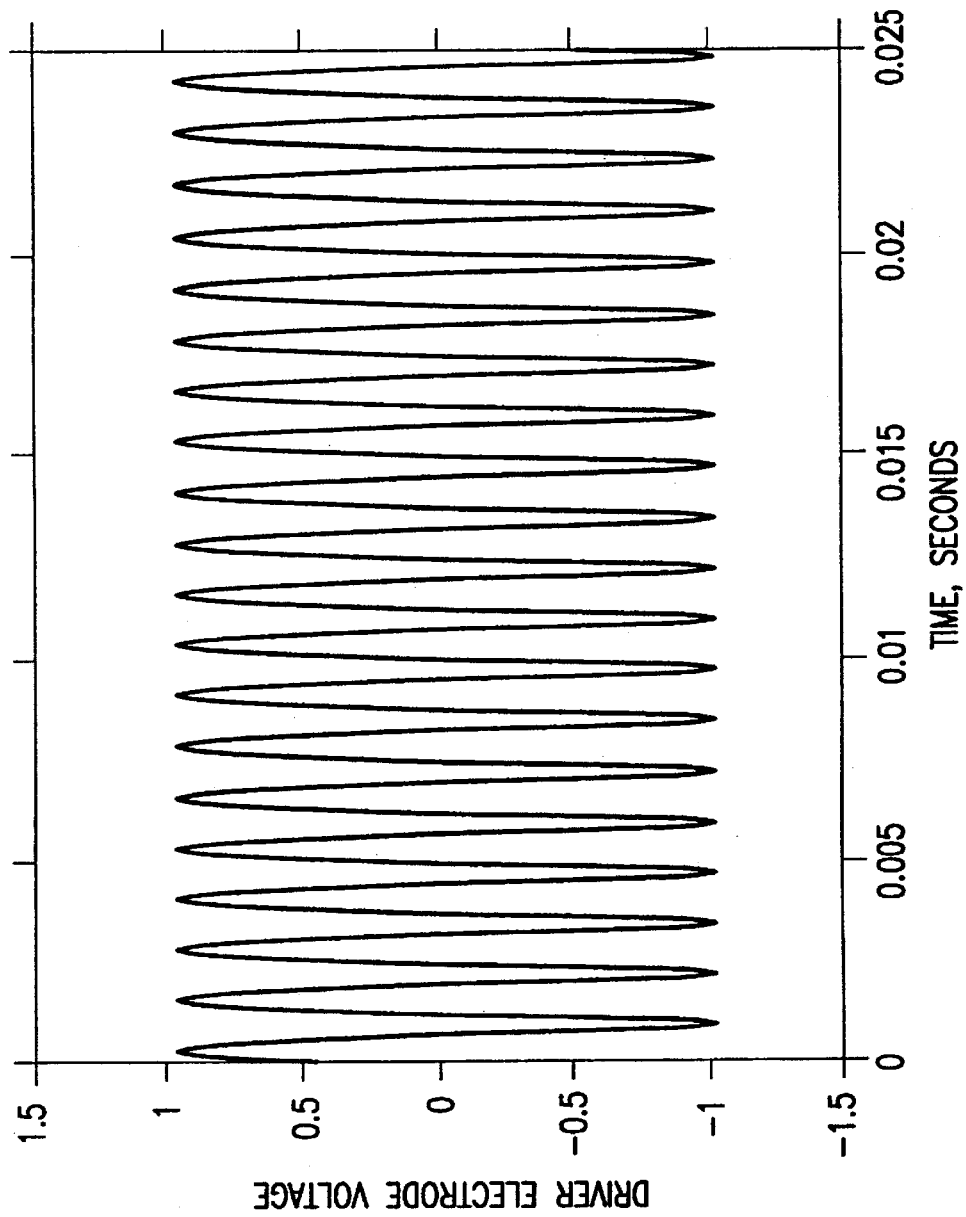

| 1.0e+004* | | |
|---|---|---|
| PEAK START | PEAK END | PEAK HEIGHT |
| 0.0106 | 0.0126 | 1.4879 |
| 0.0205 | 0.0226 | 1.2308 |
| 0.0304 | 0.0324 | 1.5662 |
| 0.0405 | 0.0423 | 1.4723 |
| 0.0506 | 0.0525 | 1.4679 |
| 0.0605 | 0.0625 | 1.6009 |
| 0.0707 | 0.0726 | 1.3767 |
| 0.0806 | 0.0826 | 1.6322 |
| 0.0904 | 0.0926 | 1.6066 |

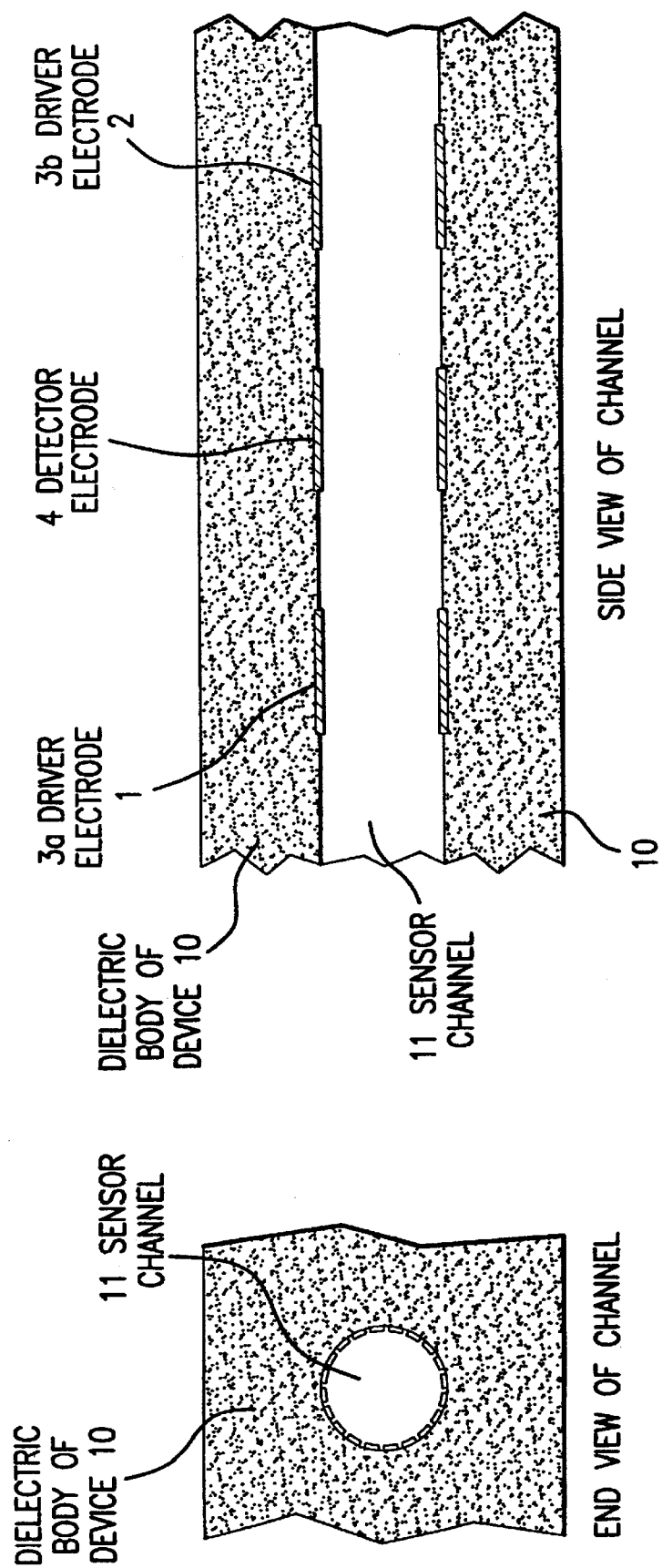

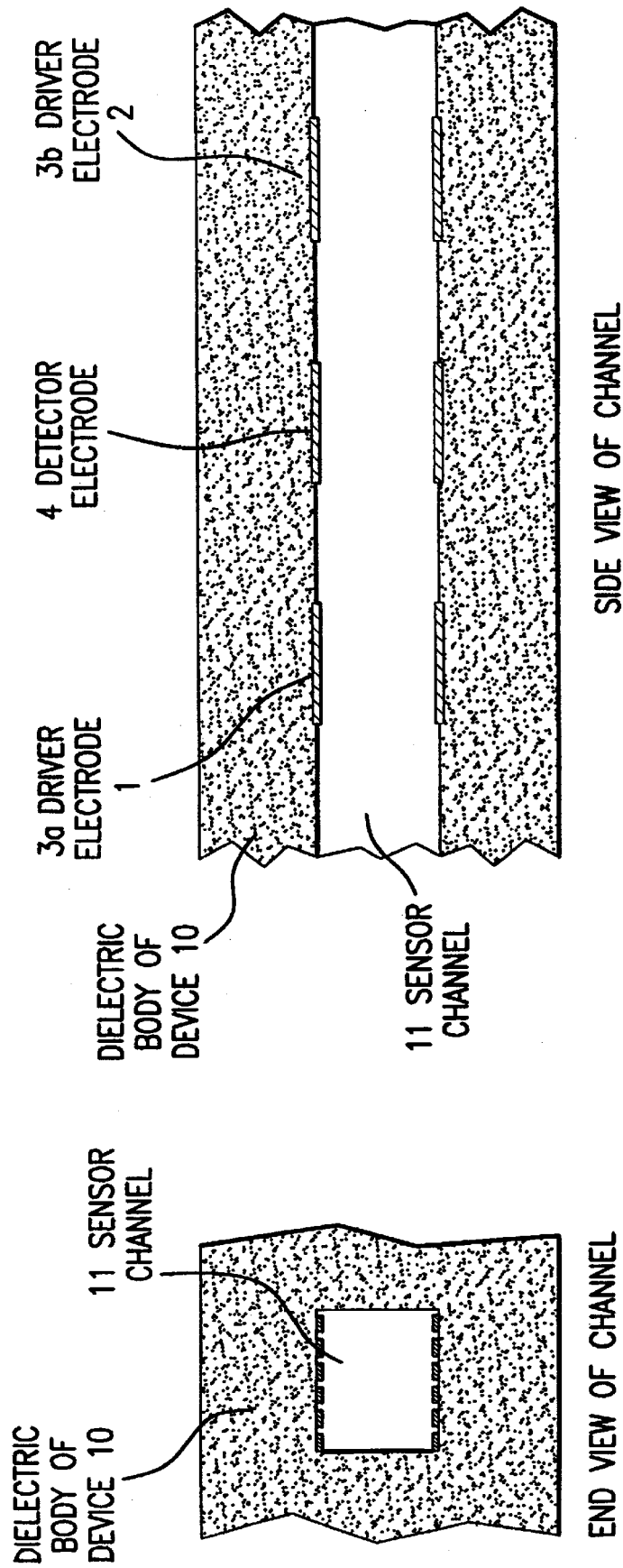
FIG.35B SIDE VIEW OF CHANNEL
FIG.35A END VIEW OF CHANNEL

PARTICLE IMPEDANCE SENSOR

The government may own rights in the present invention pursuant to the following grants: Defense Advance Research Projects Agency, Office of Naval Research; Contract No. N6601-97-C-8608; National Cancer Institute, 1 R21 CA88364-01; and Defense Advance Research Projects Agency, Army Research Office, No. DAAD10-00-1-0515.

BACKGROUND OF THE INVENTION

1. Field of the Invention

The present invention relates generally to fluidic processing and sensor technology. More particularly, it relates to a variety of apparatuses and methods for sensing particle properties in a microfluidic environment. Even more particularly, it relates to novel techniques for microfluidic, impedance sensing of particles.

2. Description of Related Art

Conventional impedance-based sensing of particles is a well-accepted method for the counting and sizing of particles and cells and finds wide application in clinical and veterinary laboratories for the analysis of blood, cell suspensions, and other samples. In operation, the technique passes a carrier fluid in which the particles to be counted are suspended through a small volume channel that usually consists of a hole in a membrane. As particles pass through the channel, the flow of electrical current between electrodes immersed in the carrier fluid on either side of the membrane is perturbed. Electronics in the circuitry that drives the electrodes detect the electrical perturbations as particles pass through the channel, and information about the size of the particles may be inferred from the characteristics of these signals. The strength of the electrical perturbation due to the presence of a particle in the channel depends approximately on the ratio of the particle volume to the channel volume and on the magnitude of the electrical current passing in the channel. Counting the electrical events that occur when a metered volume of suspending medium is drawn through the channel, and then dividing the count by the volume is done to determine the concentration of particles in a sample.

Various sensors have been developed that use impedance. U.S. Pat. No. 5,683,569, which is hereby incorporated by reference, discloses a method of sensing chemicals using a sensing material and an impedance sensor containing a channel separated from an electrode by a gap. By comparing the surface potential to the electrical impedance, the presence of a chemical species may be determined. Surface potential may be used to detect particles at low concentrations and resistance may be used to detect particles at high concentrations.

WO 9804355, which is hereby incorporated by reference, discloses a method for determining the behavior of particles in a chamber subject to a spectrum of different frequency dielectrophoretic fields. An electrical measurement is used to detect impedance fluctuations.

U.S. Pat. No. 6,149,789, which is hereby incorporated by reference, discloses a process for particle manipulation using feedback from impedance sensors. U.S. Pat. No. 6,169,394, which is hereby incorporated by reference, discloses an impedance sensor for the electrical detection of samples in a micro-analysis system; at least one pair of electrodes is used to detect the conductivity or impedance of a sample in a microchannel. Impedance sensors are also disclosed in U.S. Pat. Nos. 6,084,503, 5,569,591 and 5,580,435, each of which is hereby incorporated by reference.

Although such conventional techniques offer at least some advantage, they nevertheless include a number of significant disadvantages. While AC methods have allowed the impedances of particles to be determined at several frequencies, far greater information about the particle properties is available if more measurements over a wider range of frequencies could be accomplished for each particle. In addition, the need to accurately meter a set volume of fluid through a channel during a determination of concentrations places stringent constraints on fluid control mechanisms. This typically results in the need for a specialized fluidics platform that is often more bulky than the sensor and electronics combined. Another problem is that conventional membranes used in particle sensing are prone to blockage, necessitating accessibility for vigorous flushing. To accommodate rapid and convenient accessibility, particle impedance sensors usually take the form of benchtop instruments that are not readily adaptable to automated sample handling or in-line detection applications. Finally, the sensors of conventional instruments are often expensive and difficult to change.

The present disclosure overcomes such disadvantages through the introduction of, among other things, a membrane and the use of novel electronic detection and signal processing methods. The design and methodology of this disclosure invoke principles not previously applied to particle impedance sensor apparatuses to realize robust, multi-frequency impedance sensor capabilities that may eliminate the need for external fluid metering, permit miniaturization, allow in-line operation with other fluidic systems and instruments, and facilitate rapid and potentially automated replacement of sensor elements.

SUMMARY OF THE INVENTION

Applications of the present invention are vast and include, but are not limited to any application in which Coulter counters are used, cell and particle counting, cell and particle subpopulation analysis, cell viability analysis, cell and particle concentration analysis, cell differential analysis, medical applications, veterinary applications, bioengineering, food analysis, soil analysis, in-line particle detection in fluidic circuits and systems, detection of bacterial spores and other biological agents of potential use in warfare and terrorism, discrimination of potentially harmful biological agents from non harmful biological cells such as pollen and from inert particulate materials such as dust, smoke, and non-viable cells, detection of responses of cells such as human blood cell subpopulations to biological and chemical agents, and detection and discrimination of bacterial cells and spores (including anthrax) for medical, agricultural, environmental, and bio-warfare and bio-terrorism detection applications.

In one aspect, the invention is an impedance sensor including a sensor electrode, first and second driver electrodes, and a channel. The first and second driver electrodes are coupled to the sensor electrode and driven in counter phase to produce a net output signal of about zero at the sensor electrode. The channel is defined through the sensor electrode and the first and second driver electrodes.

In other respects, the sensor electrode may include copper. The sensor electrode may include a first and second dielectric membrane sandwiching a detector electrode. The first or second dielectric membrane may include polyimide. The first or second dielectric membrane may be laminated. The first and second driver electrodes may contact the first and second dielectric membranes, respectively. The first and second driver electrodes may be driven at multiple frequencies. The first and second driver electrodes may be driven with an alternating current signal. The cross section of the channel may be rectangular. The sensor may also include a programmable fluid processor coupled to the sensor electrode.

In another aspect, the invention is a flow-through impedance sensor including a channel, a composite membrane sensor assembly, and first and second driver electrodes. The channel is for transporting a carrier medium and particles through the impedance sensor. The composite membrane sensor assembly is coupled to the channel and includes a detector electrode sandwiched between first and second dielectric membranes. The first and second driver electrodes are coupled to the channel and are positioned adjacent opposite sides of the composite membrane sensor assembly. The first and second driver electrodes are driven in counter phase to produce: (a) a net output signal of about zero at the detector electrode when no particle is within the impedance sensor; and (b) a non-zero net output signal at the detector electrode when a particle is within the impedance sensor.

In other respects, the first and second driver electrodes may be in contact with the composite membrane sensor assembly. The first and second driver electrodes may be driven at multiple frequencies. The first and second driver electrodes may be driven with an alternating current signal. The impedance sensor may also include a programmable fluid processor coupled to the sensor electrode.

In another aspect, the invention is a method for determining a characteristic of a packet. A fluid containing a packet is flowed through an impedance sensor that includes first and second driver electrodes driven in counter phase to produce a net output signal of about zero at a sensor electrode. Perturbations of the net output signal arising from changes in impedance associated with the presence of the packet within the impedance sensor are measured. The characteristic of the packet are then determined from the perturbations.

In other respects, the characteristic of the packet may include packet size. The characteristic of the packet may include packet transit time through the impedance sensor. The characteristic of the packet may include packet velocity. The characteristic of the packet may include packet concentration. The characteristic of the packet may include a relative displacement within the impedance sensor. The characteristic of the packet may include packet impedance.

In another aspect, the invention is a method for determining a characteristic of a particle. An impedance sensor is provided including a sensor electrode, first and second driver electrodes coupled to the sensor electrode and driven in counter phase to produce a net output signal of about zero at the sensor electrode, and a channel defined through the sensor electrode and the first and second driver electrodes. A multi-frequency drive signal is applied to the first and second driver electrodes. An impedance signal is received from the sensor electrode. In-phase and out-of-phase components of the impedance signal are determined at the frequencies of the drive signal. Changes in the in-phase and out-of-phase components indicative of a particle event are detected. Portions of the impedance signal are analyzed about the particle event to determine the characteristic of the particle.

In other respects, the drive signal may include a composite of separate waveforms of different frequencies, each frequency being an integer multiple of a fundamental frequency. The drive signal may consist of 8 separate sine waves having frequencies f, 2f, 4f, 8f, 16f, 32f, 64f, and 128f. The impedance signal components may be represented as 24 bit words. The method may also include deriving a composite signal comprising a moving sum of magnitudes of changes of the in-phase and out-of-phase components. Detecting changes indicative of a particle event may include determining when the composite signal exceeds a threshold value above a noise floor. Analyzing portions of the impedance signal about the particle event to determine the characteristic of the particle may include: calculating an overlap integral, constraining curves associated with the in-phase and out-of-phase components to obey a Kramers-Kronig relationship, determining a velocity of the particle, determining a mean fluid velocity, determining a concentration of particles, determining a size of the particle, determining a relative displacement of the particle, determining a dielectric property of the particle, determining a conductivity property of the particle, determining an impedance of the particle, determining a cell membrane permittivity of the particle, and/or determining a cytoplasmic permittivity of the particle.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows a device having no particle in the sensor channel. FIG. 1B shows a device having one particle in the sensor channel.

FIG. 3A is a side view, and FIG. 3B is a top view.

FIG. 4A has no particle in the sensor channels. FIG. 4B has one particle in a sensor channel.

FIG. 9A shows top views of the structures of three individual layers. Layers I and III are dielectric membranes, and layer II is a sensor electrode. All of the dimensions and materials shown (e.g., bottom being $50\mu$ polyimide, center being $50\mu$ copper, and top being $50\mu$ polyimide) are exemplary only. FIG. 9B shows a side view of the structure after assembly. The hole all the way through the sensor assembly is the sensor channel. The larger hole that passes through only the top dielectric layer permits access to the sensor electrode through which electrical contact can be made to sensor electronics.

FIG. 20A, FIG. 20B and FIG. 20C are plots according to embodiments of the present disclosure showing the phase and strength of a sensor signal reflect the particle response (FIG. 20A) times the AC signal (shown as a single frequency sine function, FIG. 20B). The resulting sensor signal is shown in FIG. 20C.

FIGS. 34A and 34B are schematic diagrams of an impedance sensor according to embodiments of the present disclosure in which the driver and sensor electrodes are microfabricated inside a fluidic channel of circular cross section.

FIGS. 35A and 35B are schematic diagrams of an impedance sensor according to embodiments of the present disclosure in which the driver and sensor electrodes are microfabricated inside a fluidic channel of rectangular cross section.

DESCRIPTION OF ILLUSTRATIVE EMBODIMENTS

Figure 1B:
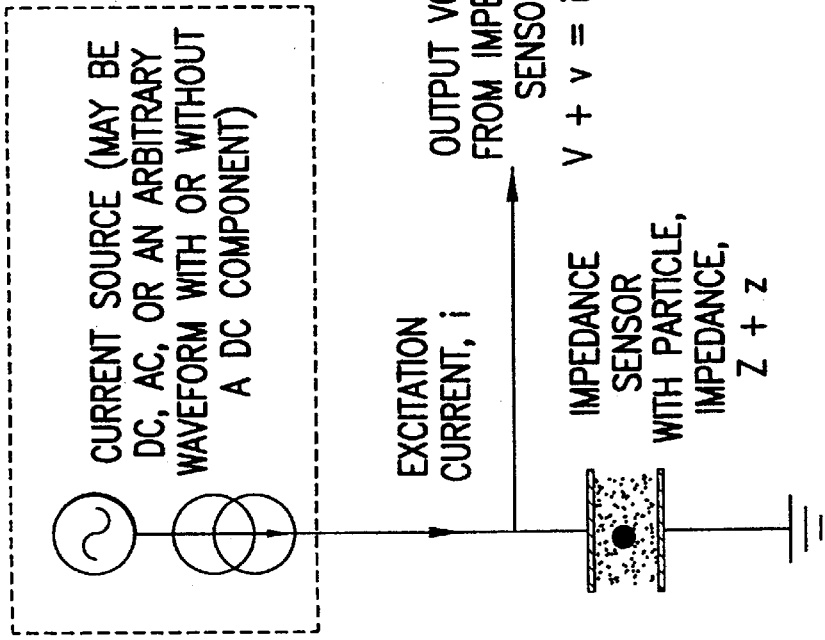
FIGS. 1A and 1B are schematic diagrams of conventional impedance sensors having a single channel.

The present disclosure overcomes deficiencies in the art by providing, in certain embodiments, a sensor that is a robust, multi-frequency impedance sensor that can be used to measure both particle characteristics and concentrations. This sensor can be used in microfluidic systems as an in-line component with other fluidic systems and instruments and the sensor element can easily be replaced. Also provided are processing methods for determining fluidic characteristics using sensor readings.

Fluidic Systems

Technology in fluidic and microfluidic systems has advanced such that there are numerous devices and systems available for the manipulation and analysis of small chemical and biological samples. As will be understood by those of ordinary skill in the art, it would be advantageous for those systems to be used with the techniques of the current disclosure.

Sensor devices of the current disclosure may be used with, for example, the apparatuses and methods described in U.S. Pat. No. 6,294,063, which is incorporated herein by reference. That patent discloses techniques that relate to the manipulation of packets of material using a reaction surface, an inlet port, a programmable manipulation force, a position sensor, and a controller. In one embodiment of that disclosure, material may be introduced onto a reaction surface with the inlet port. The material may be compartmentalized to form a packet, and the position of the packet may be tracked with the position sensor. Those of ordinary skill in the art will recognize, having the benefit of this disclosure, that techniques disclosed herein may be applied to the position sensor to allow for efficient, robust tracking of packets of material. The programmable manipulation force (which, in one embodiment, may involve a dielectrophoretic force) can be adjusted as a function of the packet's position and may be applied so that the packet is programmably moved along arbitrarily chosen paths.

Other patents and applications that may be used in conjunction with the sensor of the current invention include U.S. Pat. No. 5,858,192, entitled "Method and apparatus for manipulation using spiral electrodes," filed Oct. 18, 1996 and issued Jan. 12, 1999; U.S. Pat. No. 5,888,370 entitled "Method and apparatus for fractionation using generalized dielectrophoresis and field flow fractionation," filed Feb. 23, 1996 and issued Mar. 30, 1999; U.S. Pat. No. 5,993,630 entitled "Method and apparatus for fractionation using conventional dielectrophoresis and field flow fractionation," filed Jan. 31, 1996 and issued Nov. 30, 1999; U.S. Pat. No. 5,993,632 entitled "Method and apparatus for fractionation using generalized dielectrophoresis and field flow fractionation," filed Feb. 1, 1999 and issued Nov. 30, 1999; U.S. patent application Ser. No. 09/395,890 entitled "Method and apparatus for fractionation using generalized dielectrophoresis and field flow fractionation," filed Sep. 14, 1999; U.S. patent application Ser. No. 09/883,109 entitled "Apparatus and method for fluid injection," filed Jun. 14, 2001; U.S. patent application Ser. No. 09/882,805 entitled "Method and apparatus for combined magnetophoretic and dielectrophoretic manipulation of analyte mixtures," filed Jun. 14, 2001; U.S. patent application Ser. No. 09/883,112 entitled "Dielectrically-engineered microparticles," filed Jun. 14, 2001; and U.S. patent application Ser. No. 09/883,110 entitled "Systems and methods for cell subpopulation analysis," filed Jun. 14, 2001, each of which are herein incorporated by reference.

Yet another application that may be used in conjunction with the teachings of the current invention include those described in "Micromachined impedance spectroscopy flow cytometer of cell analysis and particle sizing," *Lab on a Chip*, vol. 1, pp. 76–82 (2001), which is incorporated by reference. For instance, methods for processing signals to determine particle concentrations and for correcting signals for particle trajectories disclosed herein may be applied to the planar electrode embodiments described in this journal article. More particularly, the methods of this disclosure may provide (a) more accurate impedance data for particles and (b) particle concentration values without the need to explicitly measure fluid flow volumes by methods outside the sensor.

In many of the systems referenced above, impedance measurements are typically used to determine certain informative characteristics of samples under study or analysis. For instance, if a dielectric medium above an electrode is displaced by a packet of material having different dielectric and/or conductive properties, the impedance detected at the electrode element will change. Thus, one may accordingly determine the position of packets by noting the impedance measurements associated therewith.

Other characteristics of packets may also be determined from the impedance detected at the electrode element. For example, the velocity of a packet flowing past an electrode may be measured by using the time difference between when the packet is above one electrode and when the same packet is above a second electrode. When the spacing between the electrodes is known, the velocity can correspondingly be determined. Since the number of packets flowing past an electrode can also be measured, the concentration of the packets can be determined directly from appropriate impedance sensors.

With the benefit of this disclosure, one of skill in the art will appreciate that the descriptions herein may be implemented in many different ways. In particular, one may use any suitable type of impedance measurement device known in the art to function with one or more electrodes. Such devices may include an impedance analyzer, a DC/AC conductance meter, or any circuit based upon methods of operation of these or other instruments having an identical or similar function.

Impedance Sensors

Figure 1A:
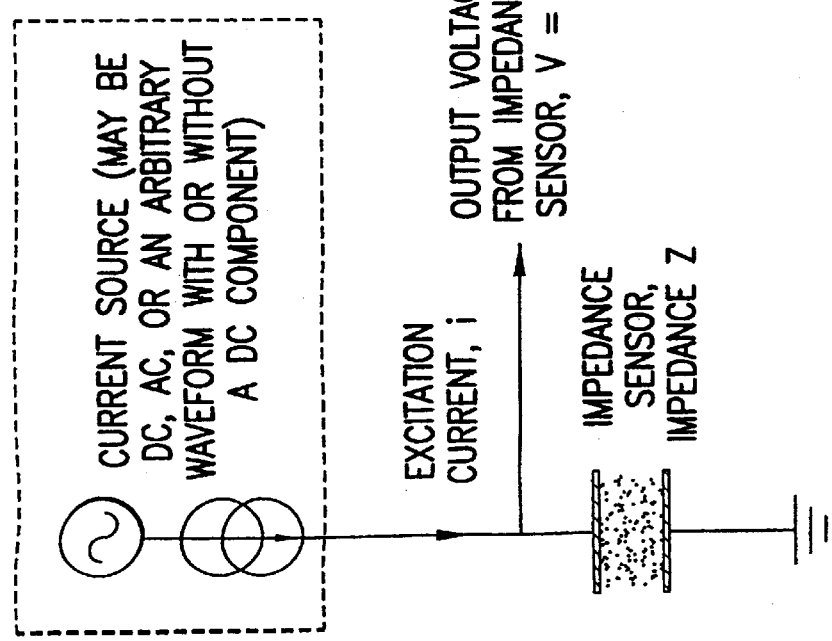

An impedance sensor can measure changes in the voltage over a cross-sectional area. A simple, conventional impedance sensor for packet characterization may include a single channel device that is excited by a current from a current generator—as shown in FIGS. 1A and 1B. A voltage develops across the sensor in proportion to the drive current and the impedance of the sensor. The current may be direct (DC excitation), an AC signal consisting of one or more sinusoidal components comprising an arbitrary waveform, or a mixture of DC and arbitrary components. When a particle enters the sensor channel, it perturbs the channel impedance, resulting in a change in the output voltage characteristics. Analysis of the voltage change allows the effective impedance of the particle to be deduced. If the driving current contains one or more AC frequencies, analysis of the voltage change allows the effective impedance of the particle to be deduced for each of those frequencies. Although this method is straightforward in principle and uses only one sensor channel, it has the disadvantage that analysis of the particle impedance information necessitates detection of a potentially small perturbation in the output voltage.

Figure 2:
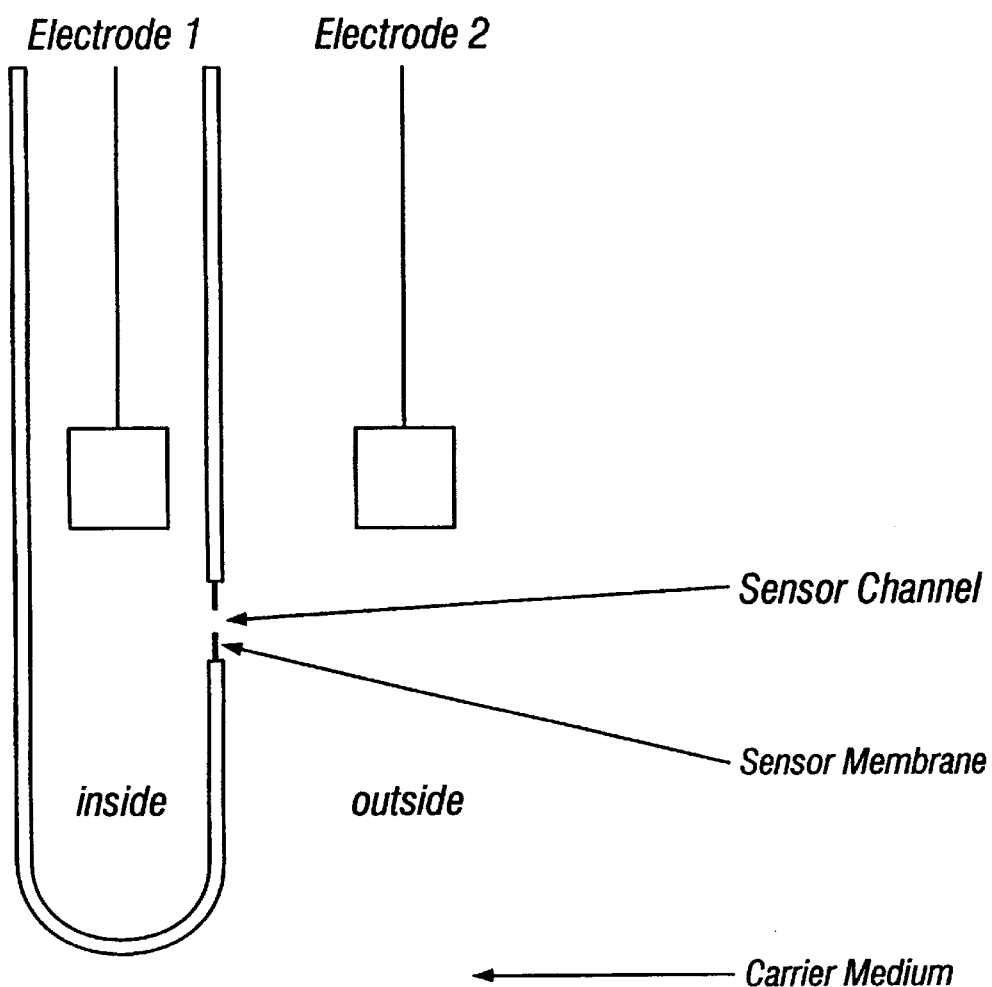
FIG. 2 is a schematic diagram showing a typical configuration of a conventional particle impedance sensor element, which may be employed in particle counters and sizers.

FIG. 2 shows a typical configuration of another conventional particle impedance sensor element, which is typically employed in particle counters and sizers. The electrical current is driven from one electrode to the other via the small hole (the sensor channel) in the sensor membrane. The impedance of the element is dominated by that of the narrow column of carrier fluid in the sensor channel. Particles are drawn into the sensor from the outside carrier medium suspension and perturb the impedance of the sensor channel as they pass through it.

Figure 3A:
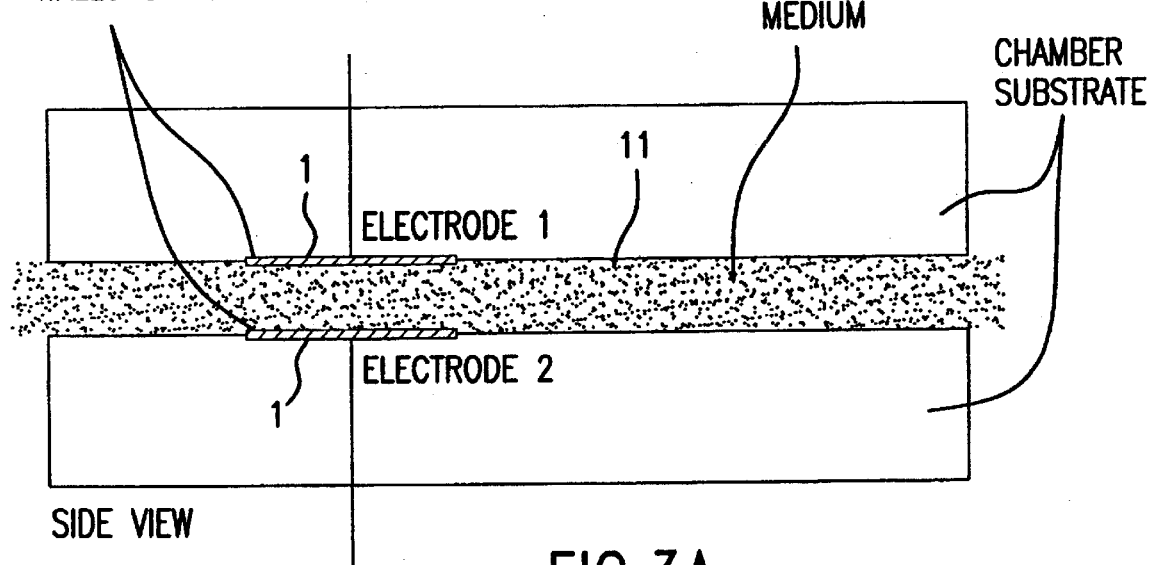
FIGS. 3A and 3B are schematic diagrams of a conventional microfabricated impedance sensor.
Figure 3B:
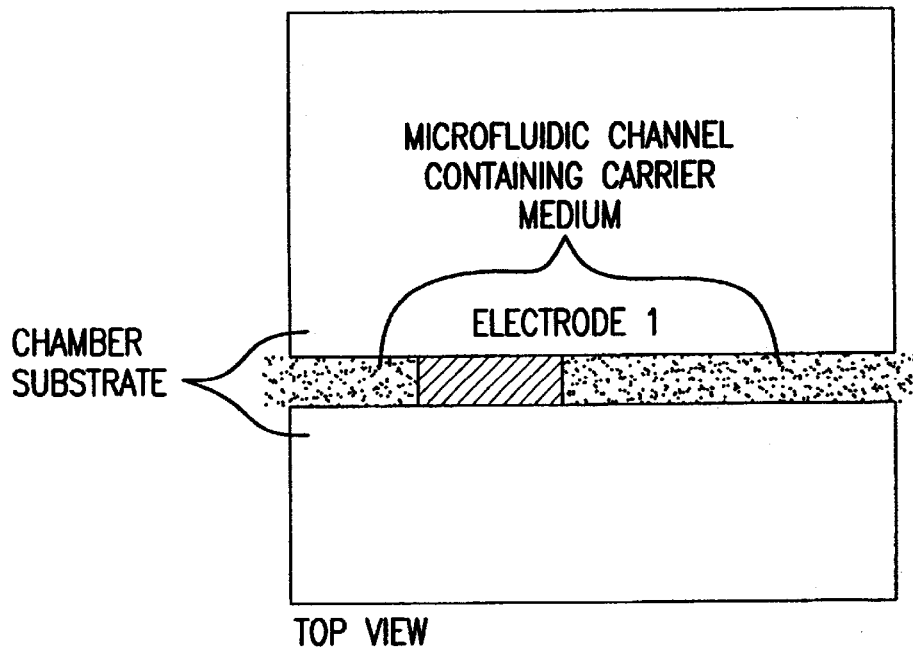

In FIGS. 3A and 3B, views of another conventional microfabricated impedance sensor are shown (FIG. 3A is a side view, and FIG. 3B is a top view). In this configuration, the requirement to achieve a high enough ratio of particle volume to sensor volume is realized by microfabricating a capillary channel 11, having facing electrodes 1 along a short section of its walls. Channel 11 contains a carrier medium. The effective volume of the sensor channel 11 is approximately equal to the volume of fluid contained within the region between the electrodes 1. Displacement of the fluid between the electrodes 1 by particles transported by the carrier medium in the microfluidic channel 11, perturbs the electrical impedance between the two electrodes.

Figure 4A:
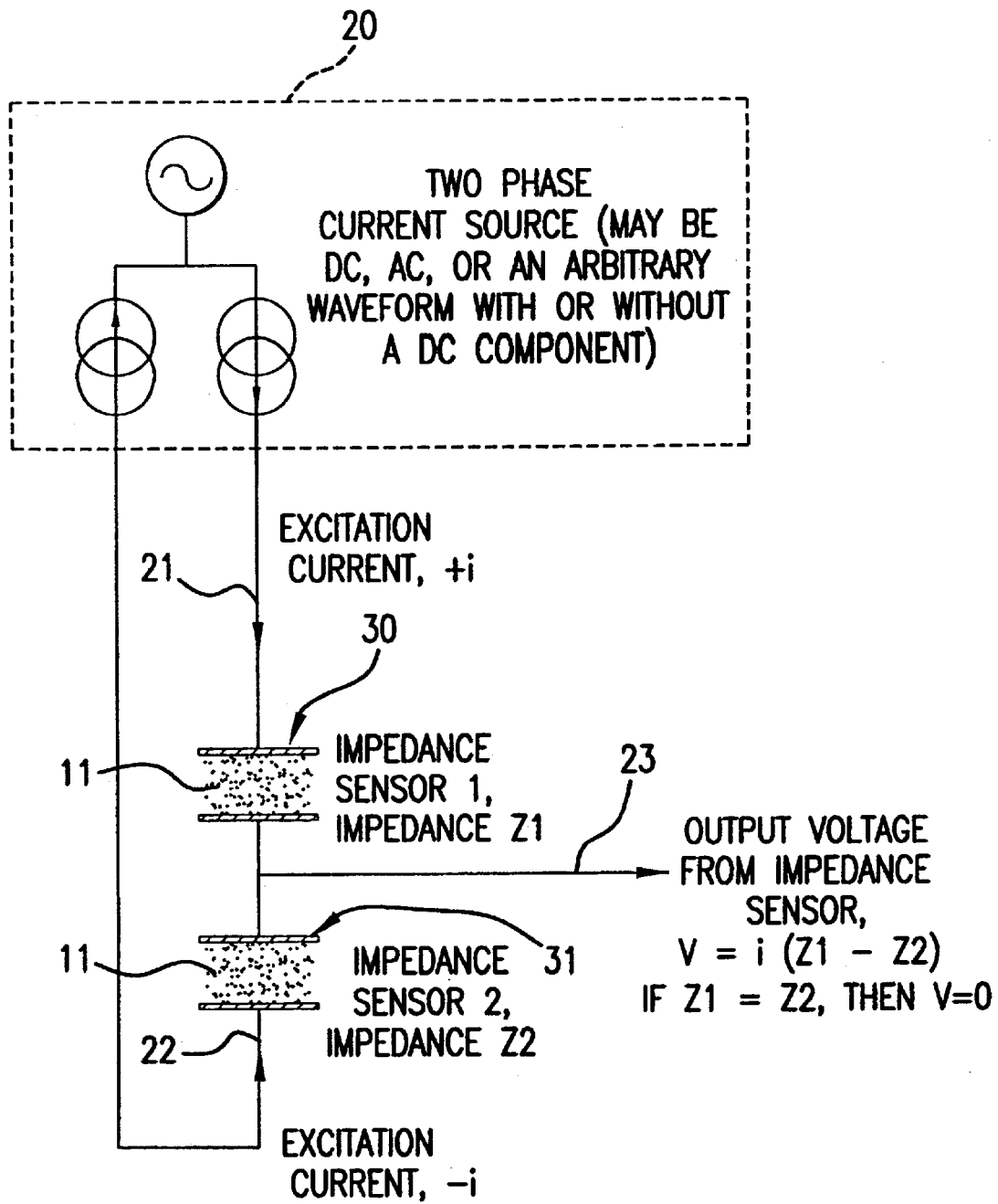
FIG. 4A and FIG. 4B are schematic diagrams showing a configuration of an impedance sensor having two channels, according to embodiments of the present disclosure.
Figure 4B:
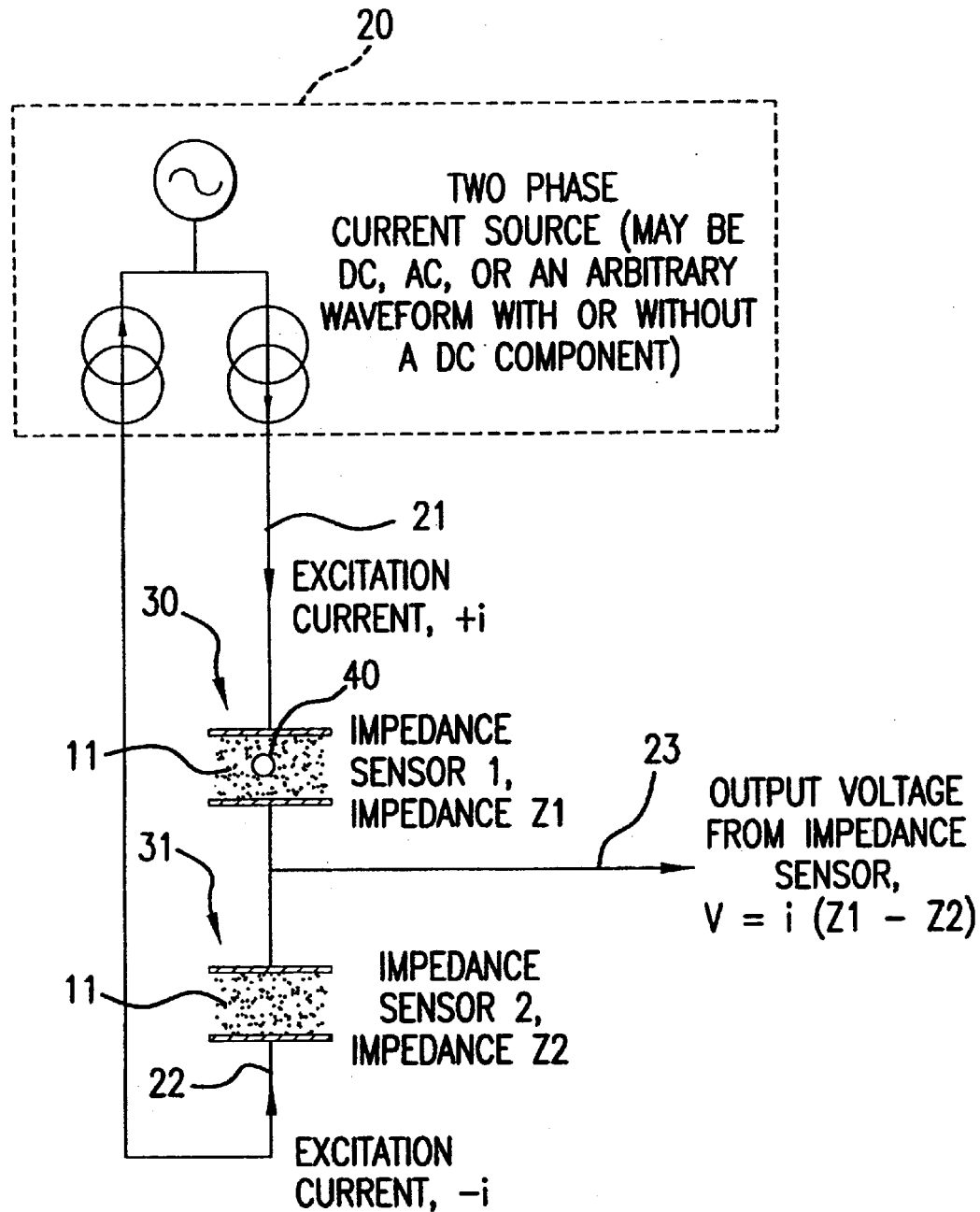

In an embodiment of the present disclosure, two channels 11, are connected and driven by identical, but opposite, current signals 21 (+i) and 22 (−i), which come from a two phase current source 20, as shown in FIGS. 4A and 4B. The output voltage 23 at the junction of the two sensors 30 and 31 with impedances $Z_1$ and $Z_2$ respectively comprises the sum of the two sensor voltages which can be given as $V=i(Z_1-Z_2)$. When the two sensors 30 and 31, have identical impedance, the output voltage 23 is zero (i.e., if $Z_1=Z_2$, then V=0). Particles are typically passed through only one of the sensor channels 30, and the other channel 31 is the reference channel. When a particle 40 enters sensor channel 30 (FIG. 4B), the impedance of only that channel is perturbed. This destroys the balance in the channels, and the output voltage 23 deviates from zero. This scheme therefore provides an output signal 23 that reflects only the sample impedance.

In practice, the output signal 23 also contains voltages resulting from imperfections in the initial matching of the sensors and their drive circuits. Nevertheless, signal processing is greatly simplified by canceling almost all of the voltage from each sensor channel. The circuit is symmetrical, and particles that pass through channel 31 will result in an output voltage of opposite phase from that caused by particles travelling through channel 30.

Figure 5:
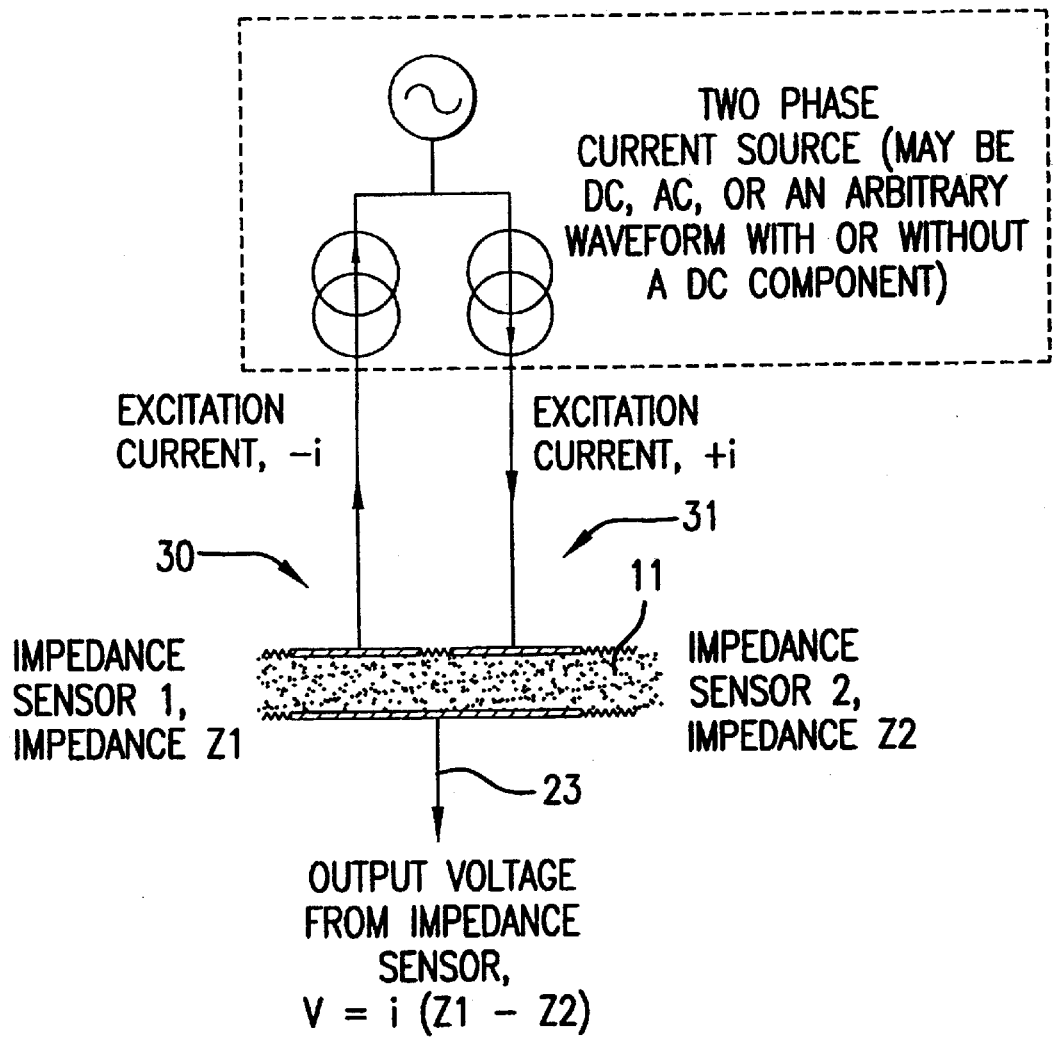
FIG. 5 is a schematic diagram of a configuration of an impedance sensor having one channel and two sensors connected to the channel, according to embodiments of the present disclosure.

In a variation of the two-sensor method and according to another embodiment of this disclosure, the two sensors may be connected in the same flow path 11, as shown in FIG. 5. In this case, the ability to balance the impedance of the sensors is enhanced because they are in the same microfluidic channel 11 and filled by the same carrier fluid. As before, the output of voltage of the sensor 23 is, in the absence of imperfections in the sensor and the drive circuitry, summed to zero. Particles that enter the first sensor 30 produce an imbalance in the circuit that produces a signal +v. When the particles are carried downstream by the fluid and enter the second sensor 31, the sample particles produce a signal −v. The method can result in ambiguous signals unless it is possible to track each particle as it passes from one sensor to the next. This, despite its great advantages over conventional techniques, may prove problematic if the sensors are far apart.

Figure 6:
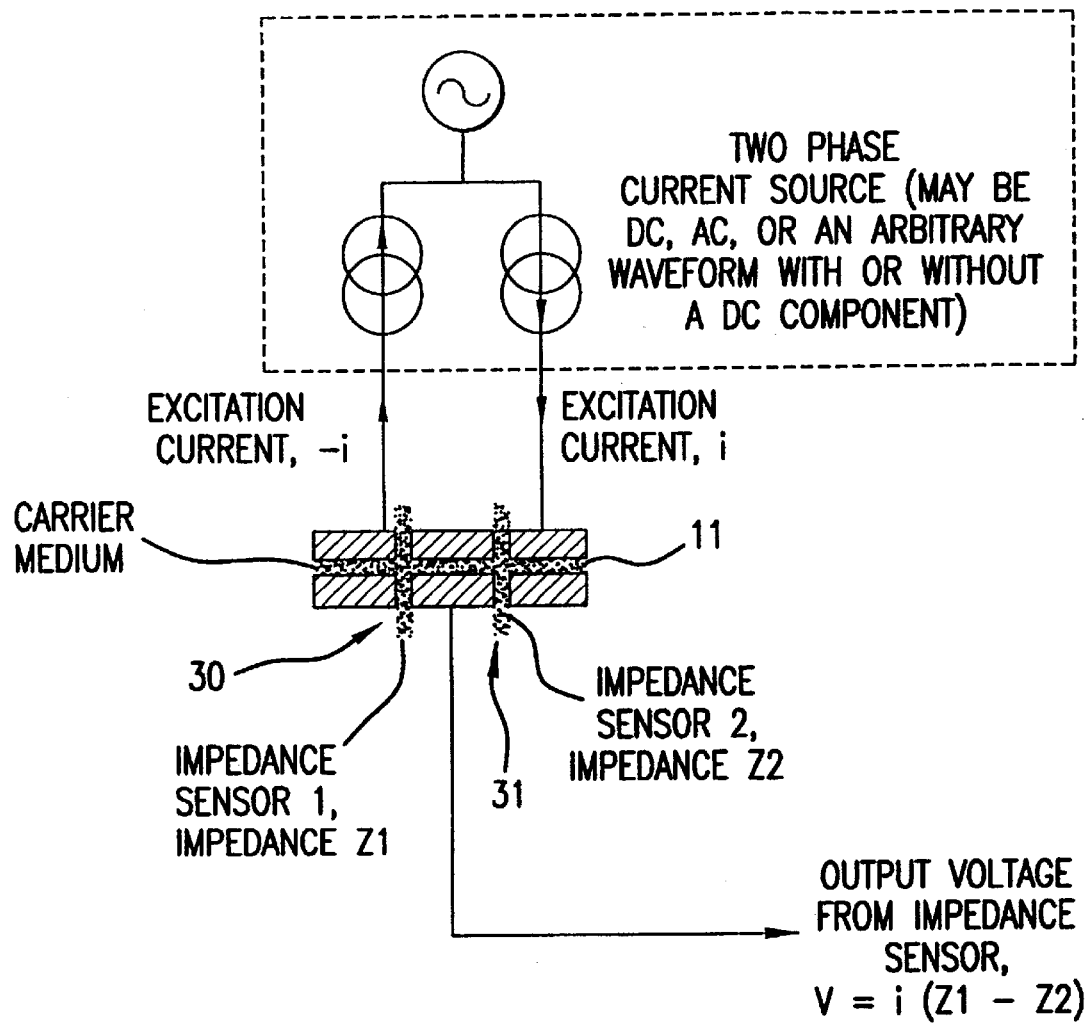
FIG. 6 is a schematic diagram of a configuration of an impedance sensor having one channel and two sensors connected to the channel in close proximity to each other such that a particle will pass both sensors before a second particle reaches the first sensor, according to embodiments of the present disclosure.

In a refinement of the two sensors, inline method, the two sensors can be brought very close together so that it becomes possible to observe each particle as it passes through both impedance sensor 30 and impedance sensor 31 before a second particle enters impedance sensor 30, as demonstrated in FIG. 6. This can be accomplished by microfabricating the two sensors in close proximity within a capillary tube 11. The small separation between the two sensor electrodes required for tracking particles as they pass from one sensor to the next may be, in certain embodiments, less than 500 µm, 400 µm, 300 µm, 200 µm or less than 100 µm. Those of ordinary skill in the art will recognize, however, that other separations will also be suitable.

In another method of forming the inline sensor, the fluid channel 11 can be formed through the electrodes, and the sensor membranes and the electrodes that are connected to the output 23 to sum the voltages from the two sensors 30 and 31 can be combined into a single electrode, effectively hybridizing the two sensors. This not only simplifies fabrication, but from an electrical standpoint confers the advantage that the electrode on which the output voltage is sensed can be made smaller. Further, it is effectively sandwiched between the electrodes to which the excitation signals are provided, having the advantageous effect of shielding it from electrical noise carried through the conductive carrier medium.

Figure 7:
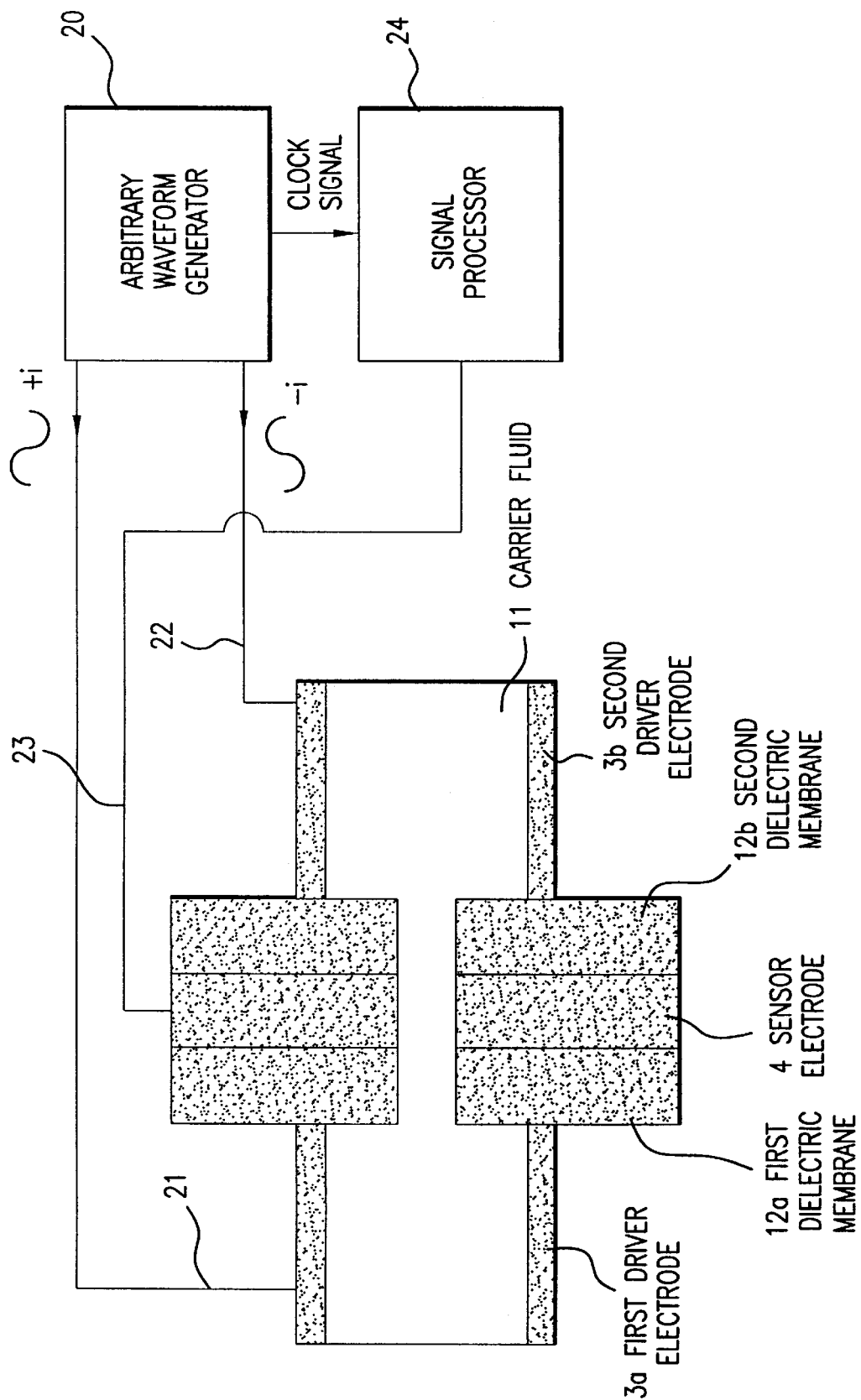
FIG. 7 is a cross sectional view of a sensor based on a two-sensor, hybrid design, according to embodiments of the present disclosure.

FIG. 7 shows a cross sectional view of an embodiment of an impedance sensor where the design of the sensor channel is based on a two-sensor, hybrid design. The sensor electrode 4 is surrounded by two dielectric membranes 12, where a first dielectric membrane is indicted by 12a and a second dielectric membrane is indicated by 12b. The two dielectric membranes 12, and the sensor electrode 4, together form a composite membrane sensor assembly. Although each of the electrodes 3 and 4, and membranes 12, appear to be segmented into a top and bottom half by the fluid channel 11 in the diagram, in reality they are situated as shown in the different viewpoint of FIG. 8. Driver electrode 3a and driver electrode 3b are excited by electrical signals of opposite phase 21 and 22 from an arbitrary waveform generator 20 programmed to provide a waveform consisting of the sum of one or more sinusoidal waves of known frequencies and phases. Because of the symmetrical construction of the sensor membrane 12, the signals from the driver electrodes 3 cancel at the sensor electrode 4 to provide a zero signal to the detector 24 when there is no particle in the channel. However, when a particle 40 (see FIG. 10) enters the channel 11, it disturbs the electrical symmetry, causing a net signal to appear on the sensor electrode 4. This signal 23 is detected and analyzed by the signal processing electronics 24. The signal 23 depends upon the position of the particle 40 in the channel 11 and it changes as the particle 40 is carried through the channel 11 by fluid flow. The nature of an exemplary signal is discussed and described in FIG. 12.

Figure 8B:
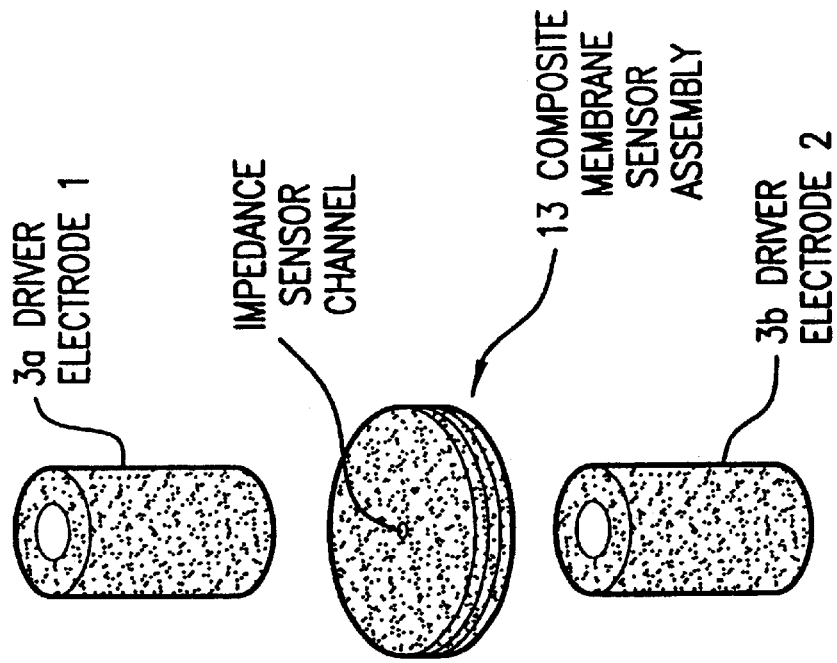
FIGS. 8A and 8B are exploded diagrams of a particle impedance sensor showing the driver electrodes, sensor electrodes and dielectric membranes, according to embodiments of the present disclosure.
Figure 8A:
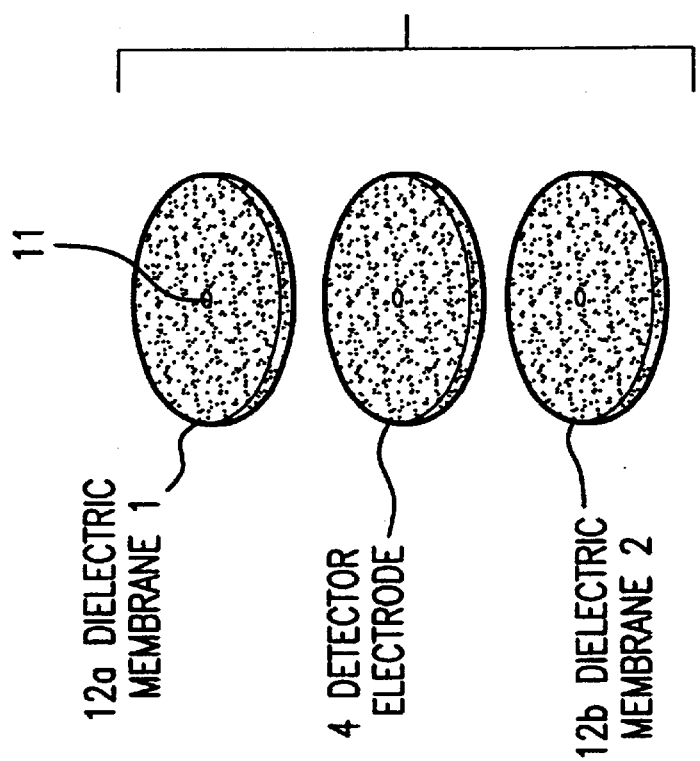

FIGS. 8A and 8B show an exploded diagram of the particle impedance sensor of FIG. 7, showing the driver electrodes 3, sensor electrode 4, and dielectric membranes 12. The fluid flow path to and from the composite membrane sensor assembly 13 occurs via channel 11 through the driver electrodes 3. The impedance sensor channel 11 is a small hole bored through the composite membrane sensor assembly 13. In operation, the fluid flow path may be completed with tubing, and the driver electrodes 3 may be mounted close to, or in contact with, the dielectric membranes 12 of the composite membrane assembly 13.

Figure 9A:
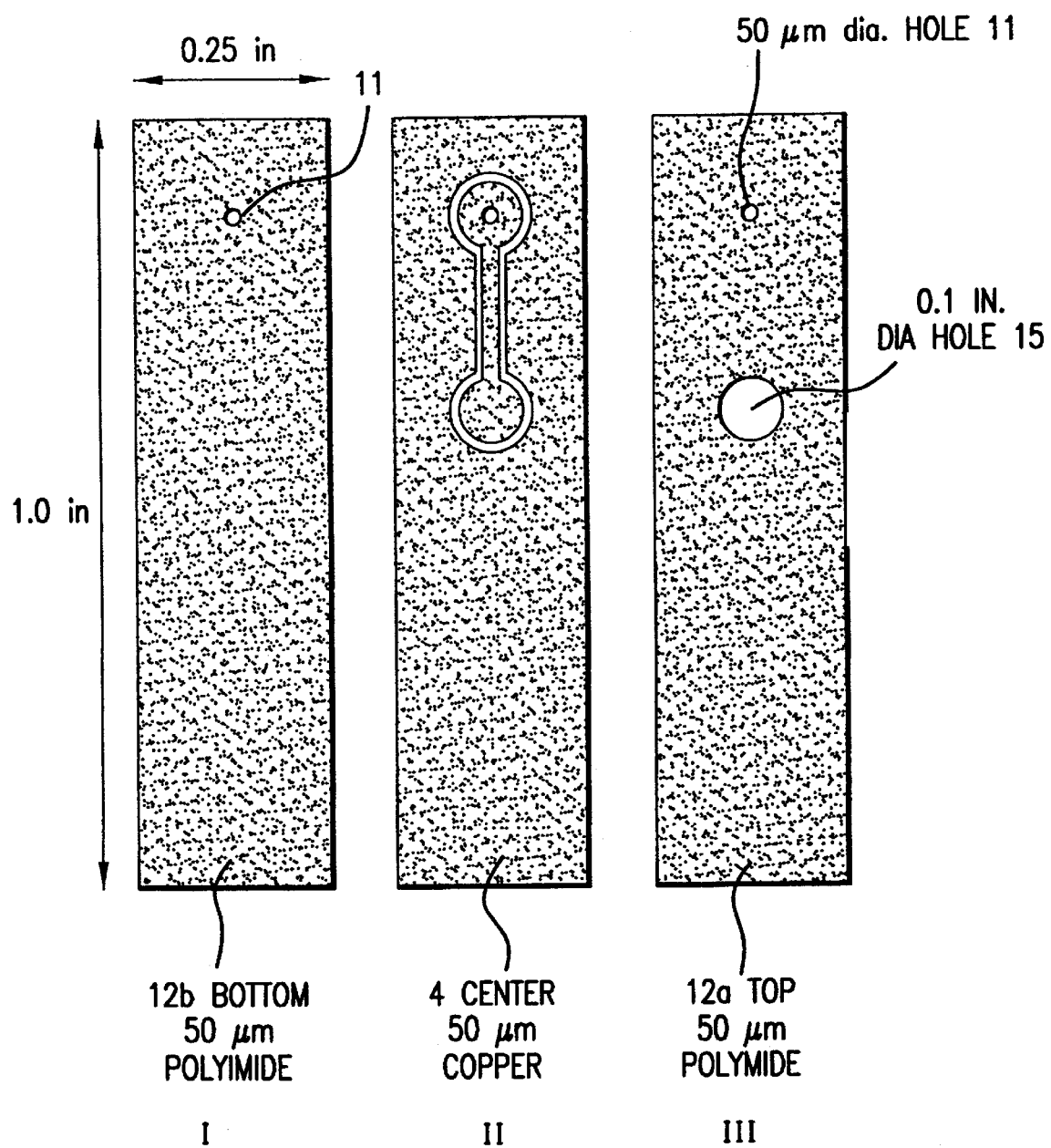
FIG. 9A and FIG. 9B are schematic diagrams of an embodiment of a particle impedance sensor according to the present disclosure.
Figure 9B:
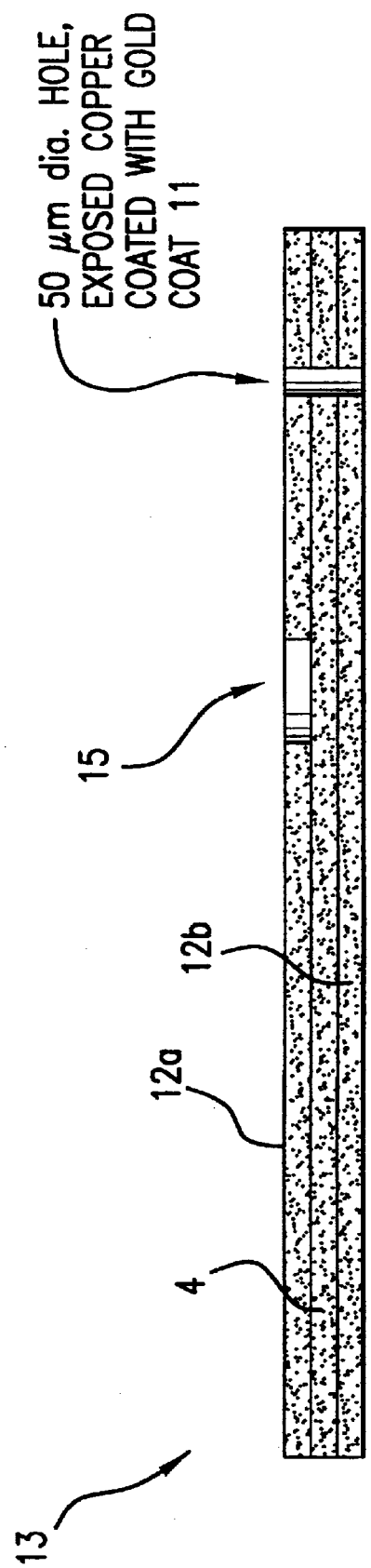

Two views of an assembled, three-layered composite sensor 13 according to embodiments of this disclosure are shown in FIGS. 9A and 9B. The channel 11, going all the way through the sensor assembly, is the sensor channel. The larger hole 15 that passes through only the top dielectric layer 12b permits access to sensor electrode 4, through which electrical contact may be made to the sensor electronics.

Particle Position

Figure 10:
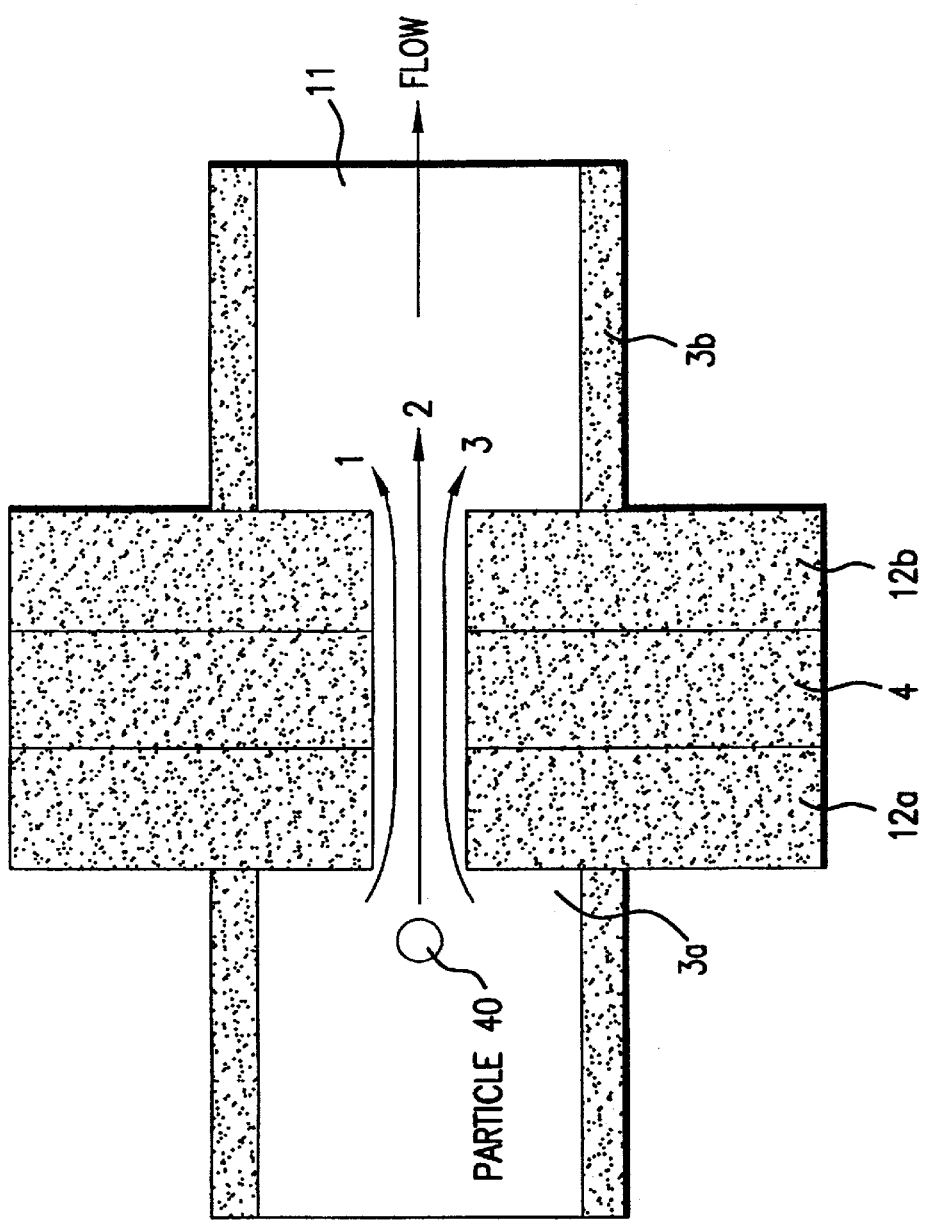
FIG. 10 is a schematic diagram showing a flow pattern of a particle carried through a sensor channel by flow of the suspending medium, according to embodiments of the present disclosure.

Particles 40 may be carried through sensor channel 11 by the flow of a suspending medium, as demonstrated by FIG. 10. Particles 40 may move along different trajectories through the channel 11 in accordance to their entry point. Trajectories 1, 2 and 3 correspond to three different entry points for the particles. The perturbation to the electrical symmetry caused by the presence of the particle 40 will vary with particle position in the channel, and different signals will result on the sensing electrode 4 from the passage of particles travelling along different trajectories. For example, particles that enter the channel close to the edge of the channel will have a greater effect on the impedance detected at the electrode than a particles that enter the channel near the centerline (a horizontal line through the midpoint of the sensor channel).

Figure 11:
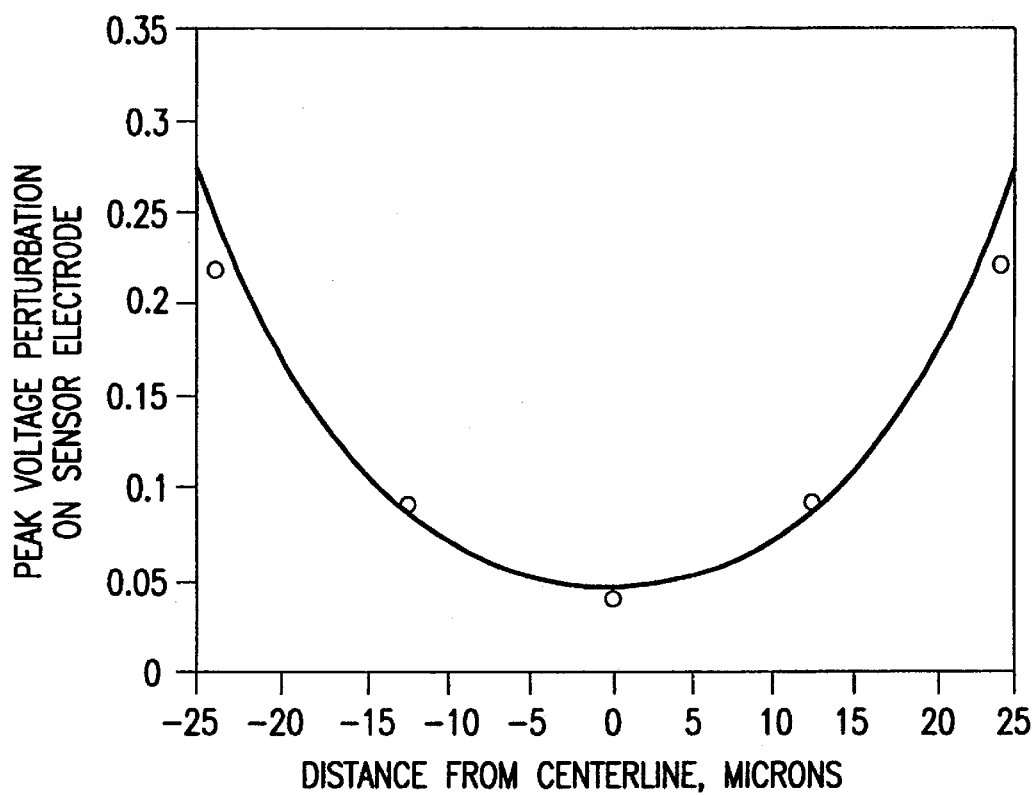
FIG. 11 is a plot of the peak of voltage perturbation on an sensor electrode produced by a 10 $\mu$m diameter particle as a function of its distance from the center of the sensor channel, according to embodiments of the present disclosure. The line shows a fit of the hyperbolic cosine function to the data.

The peak of voltage perturbation produced by a particle of 10 µm diameter passing through the impedance sensor as a function of its distance from the centerline is given in FIG. 11. The circles show the peak perturbations determined from finite element analysis for a 10 µm diameter sphere of conductivity 1.5 S/m carried in a suspending medium of conductivity 100 mS/m with a drive voltage of −10 V and +10 V.

Finite Element Simulations

Figure 12:
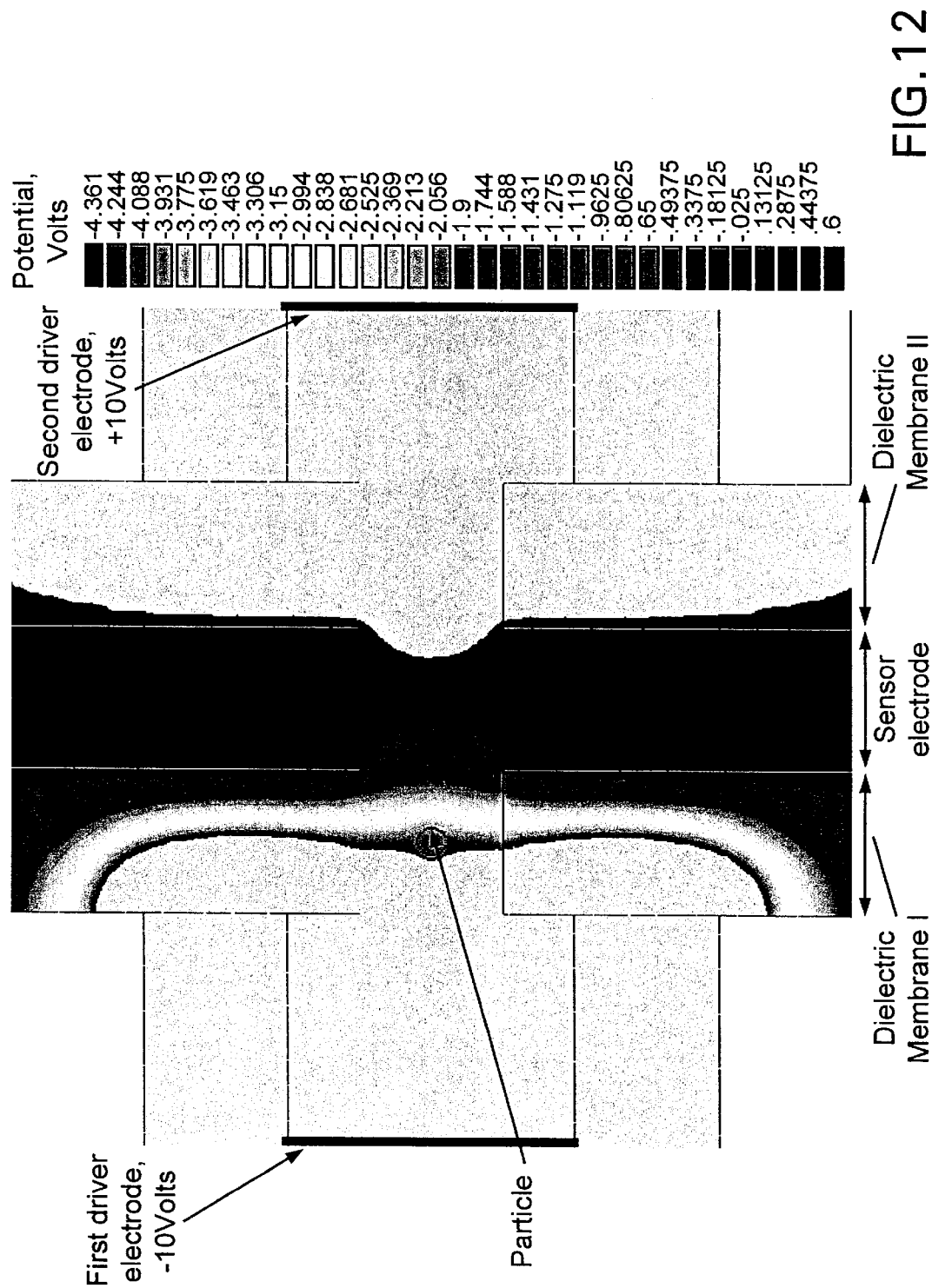
FIG. 12 is a finite element simulation showing the effect of a particle on the electrical potential distribution in a two membrane impedance sensor, according to embodiments of the present disclosure.

To determine the effect of a particle on the electrical potential distribution in an impedance sensor, a finite element simulation was done (FIG. 12). In this example, a sensor having a sensor electrode sandwiched between two dielectric membranes was used. The driver electrodes on either side of the composite membrane sensor assembly were driven at −10 V and +10 V. The particle is located on the horizontal center line of the channel half way through the first dielectric membrane 12a. In the absence of the particle 40, the potential on the sensor electrode 4 is zero but the presence of the particle 40 perturbs the potential as shown. This perturbation depends upon the particle position in the sensor channel 11. Finite element analyses like this may be used to calculate the response of the sensor for different particle positions and different sensor and driver geometries.

Figure 13A:
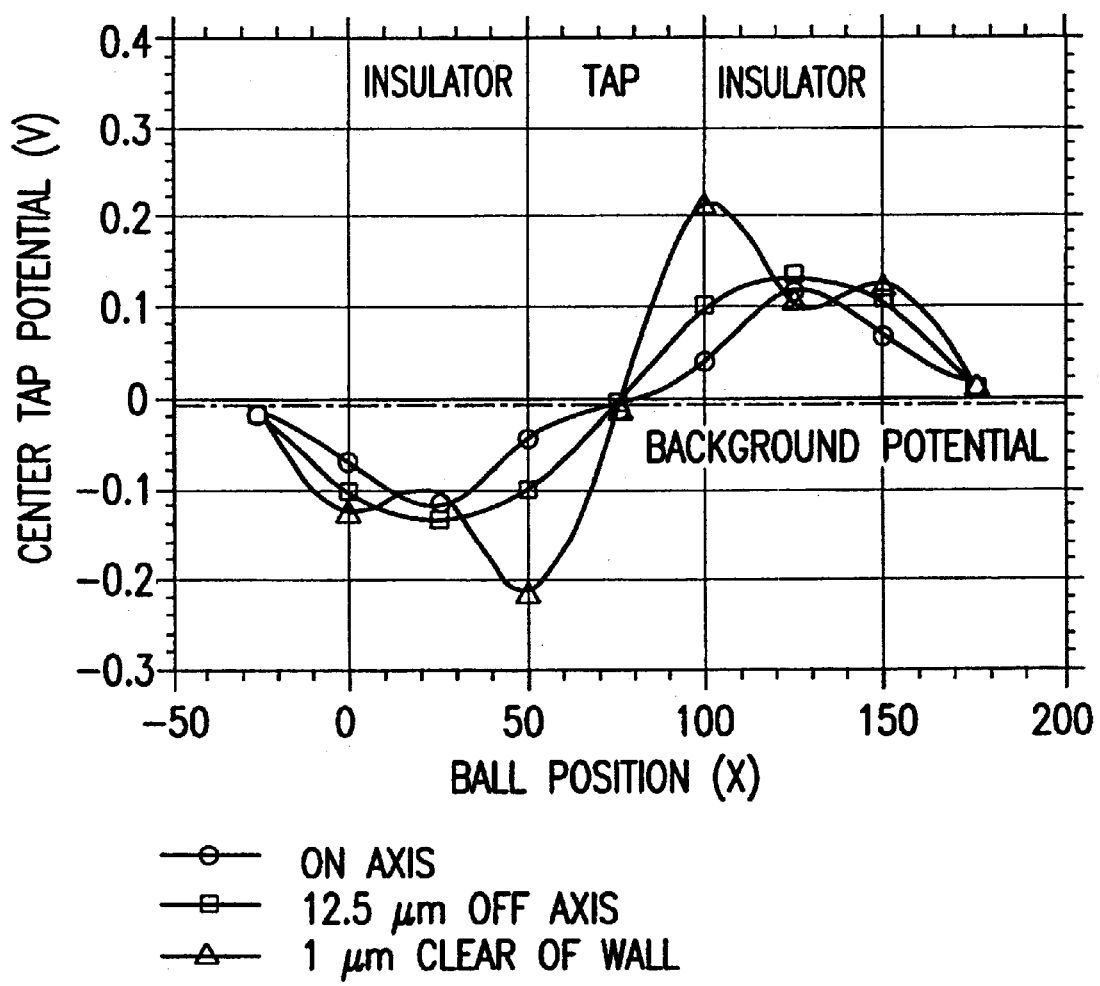
FIG. 13A and FIG. 13B are plots of sensor electrode potential where the potential perturbation is produced by a packet that is 15 times more conductive (FIG. 13A) and 1000 times less conductive (FIG. 13B) than the medium filling the channel, according to embodiments of the present disclosure.
Figure 13B:
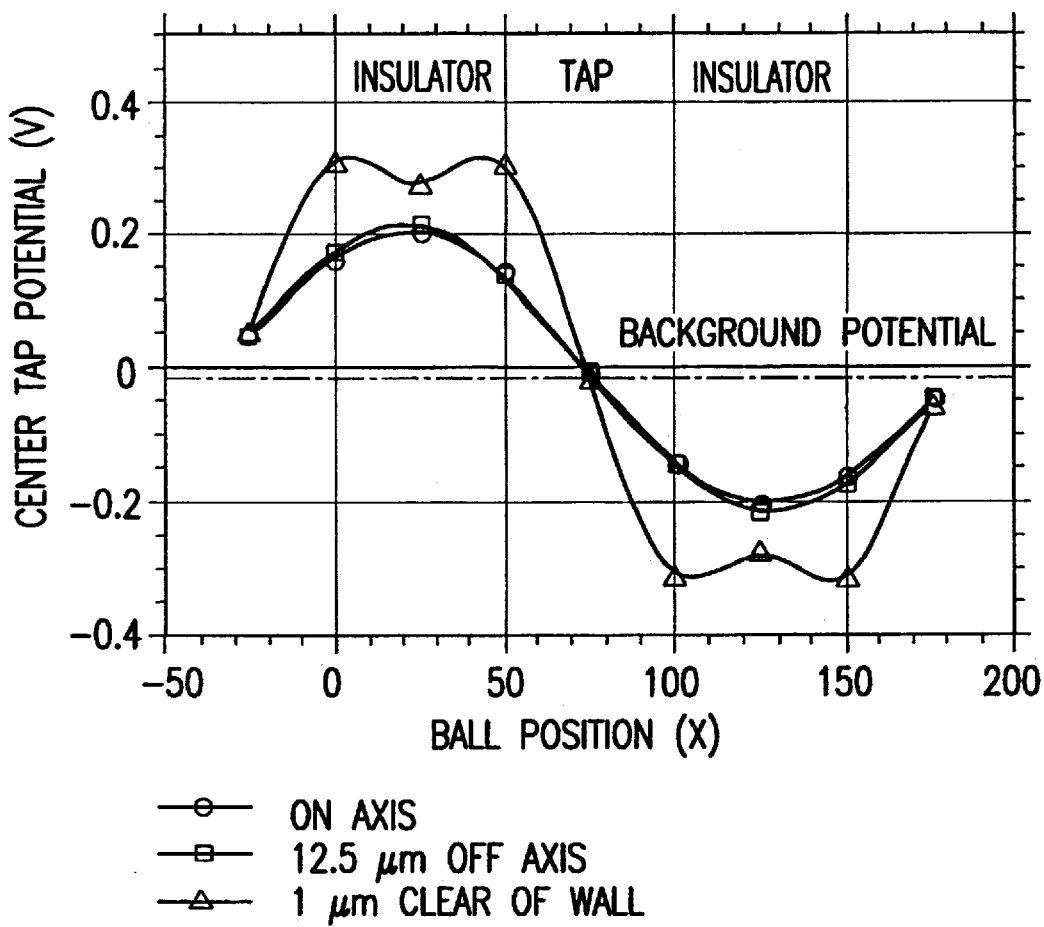

FIGS. 13A and 13B depict plots of a sensor electrode potential, determined from finite element analysis as shown in FIG. 12, as a function of particle positions in the sensor channel ranging from 25 µm to the left of the first dielectric membrane 12a to 25 µm to the right of the second dielectric membrane 12b. A packet position of 75 µm corresponds to the center of the channel in the horizontal (x) direction. Three curves are shown for particles positioned at different distances from the horizontal center line (axis) of the channel. FIG. 13A corresponds to the potential perturbations produced by a packet that is 15 times more conductive than the medium filling the channel. FIG. 13B correspond to a packet that is 1,000 times less conductive than the medium filling the channel. The channel height was 50 μm and the thickness of the dielectric membranes and the sensor electrode were 50 μm. The conductivity of the medium in the channel was 1100 mS/m. It is apparent from this data that the signal produced by the impedance sensor when a packet moves through it depends on the trajectory of the packet. Therefore, it is necessary to deduce the packet position in order to infer impedance information about the packet from the impedance sensor data.

Particle Velocity

Figure 14:
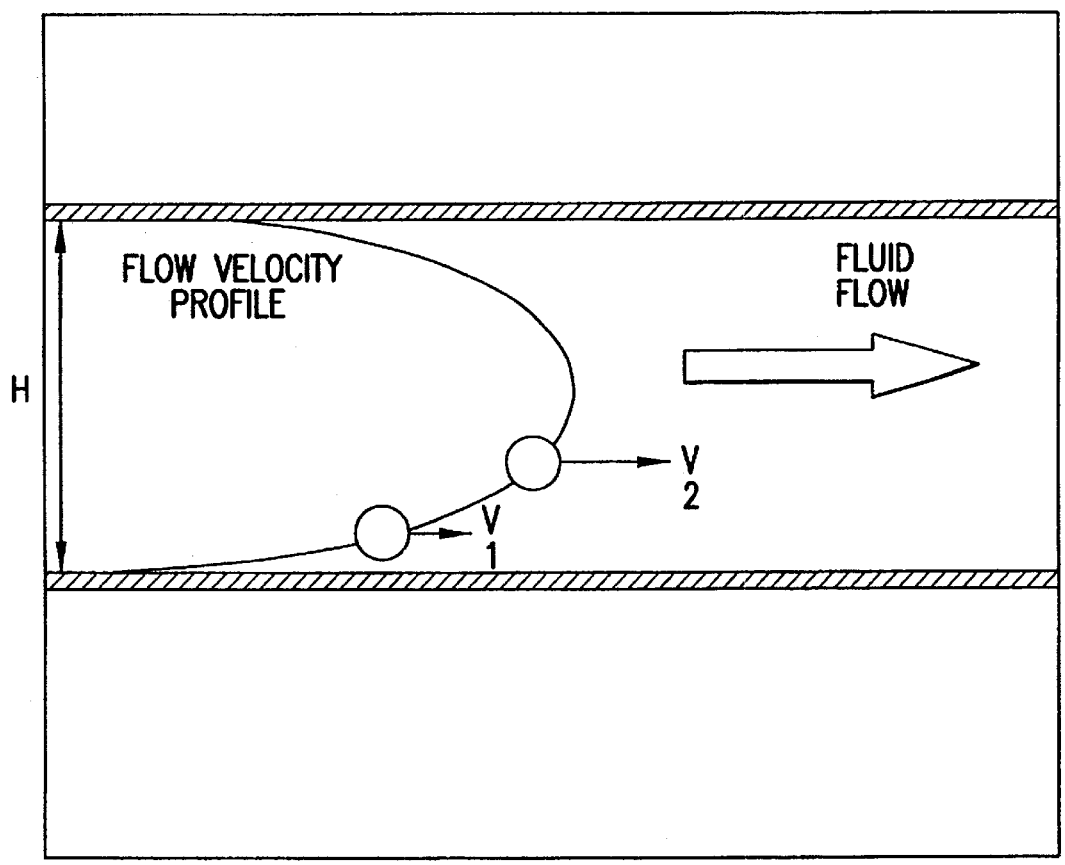
FIG. 14 shows a flow velocity profile under laminar flow conditions, according to embodiments of the present disclosure.

When fluid flows through a channel under laminar flow conditions, or conditions where the flow through the channel is slow enough so as not to cause turbulence (referred to as at low Reynolds numbers in hydrodynamics), a flow velocity profile develops such that the fastest fluid flow occurs at the center of the channel and the lowest velocity occurs at the walls of the channel. Consequently, particles that travel through the channel under the influence of laminar fluid flow will be carried at velocities that accurately reflect their position in the fluid flow profile. FIG. 14 depicts two particles traveling along trajectories at different distances from the channel walls. These particles are being carried at two different velocities. If the speed that an arbitrary particle travels in the channel is known, its position relative to the channel walls can be inferred from a knowledge of the flow velocity profile. In simple geometries, the flow profile can be calculated using simple equations. In more complex geometries, finite element or other modeling methods can be used to calculate the fluid flow profile distribution.

Figure 15:
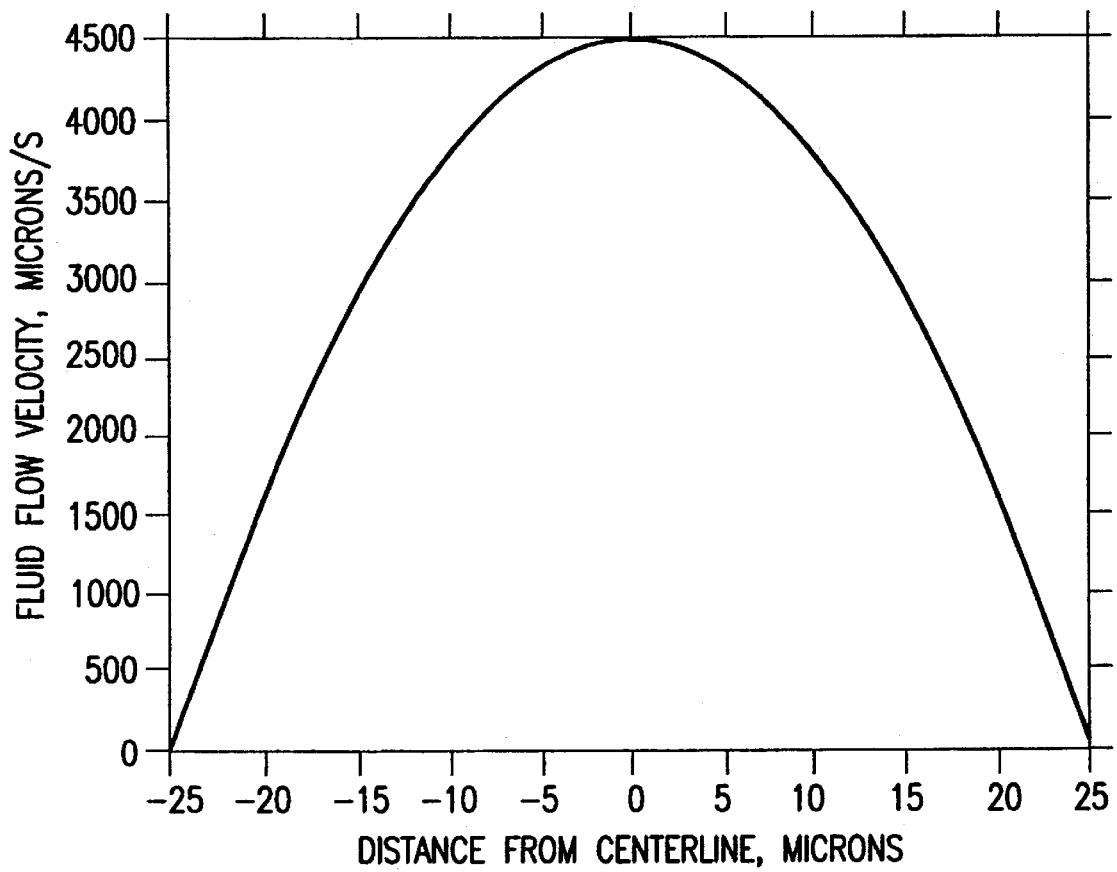
FIG. 15 is a plot of velocity of a carrier medium in a sensor channel as a function of the distance from the centerline for a parabolic flow profile, according to embodiments of the present disclosure.

The velocity of the carrier medium in the sensor channel can be given as a function of the distance from the centerline for a parabolic flow profile in FIG. 15. This profile pertains when the channel is sufficiently long, and the fluid is flowing sufficiently slowly to assure that laminar flow conditions prevail. Under these or other conditions, the flow profile may be simulated using finite element or other methods. In FIG. 15, the channel height (H) is assumed to be 50 μm and the mean flow velocity $v_0$, the velocity distance x from the channel wall for a rectangular channel is given by $$v = 6 * v_0 * \frac{x}{H}\left(1 - \frac{x}{H}\right).$$

Figure 16:
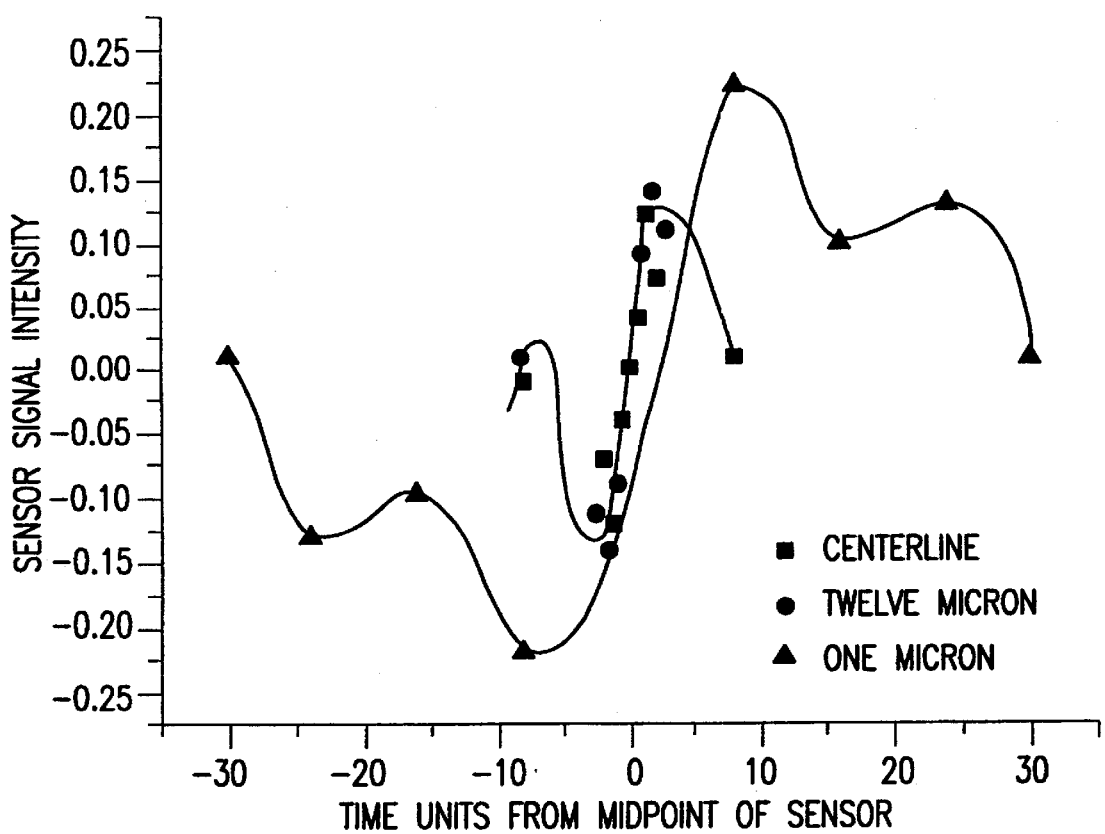
FIG. 16 is a plot showing pulse shapes for particles carried by a carrier medium having a parabolic flow profile as they pass through a sensor, according to embodiments of the present disclosure.

FIG. 16 describes pulse shapes for particles carried by a carrier medium having a parabolic flow profile as they pass through the sensor along three trajectories parallel to the centerline calculated by scaling the horizontal axis of the finite element simulation results shown of FIG. 12 to allow for the relative flow rates corresponding to their position in the channel. In general, fits to data like this can be used to derive characteristic curves for the behavior of the sensor channel.

Sample Analysis

Figure 17:
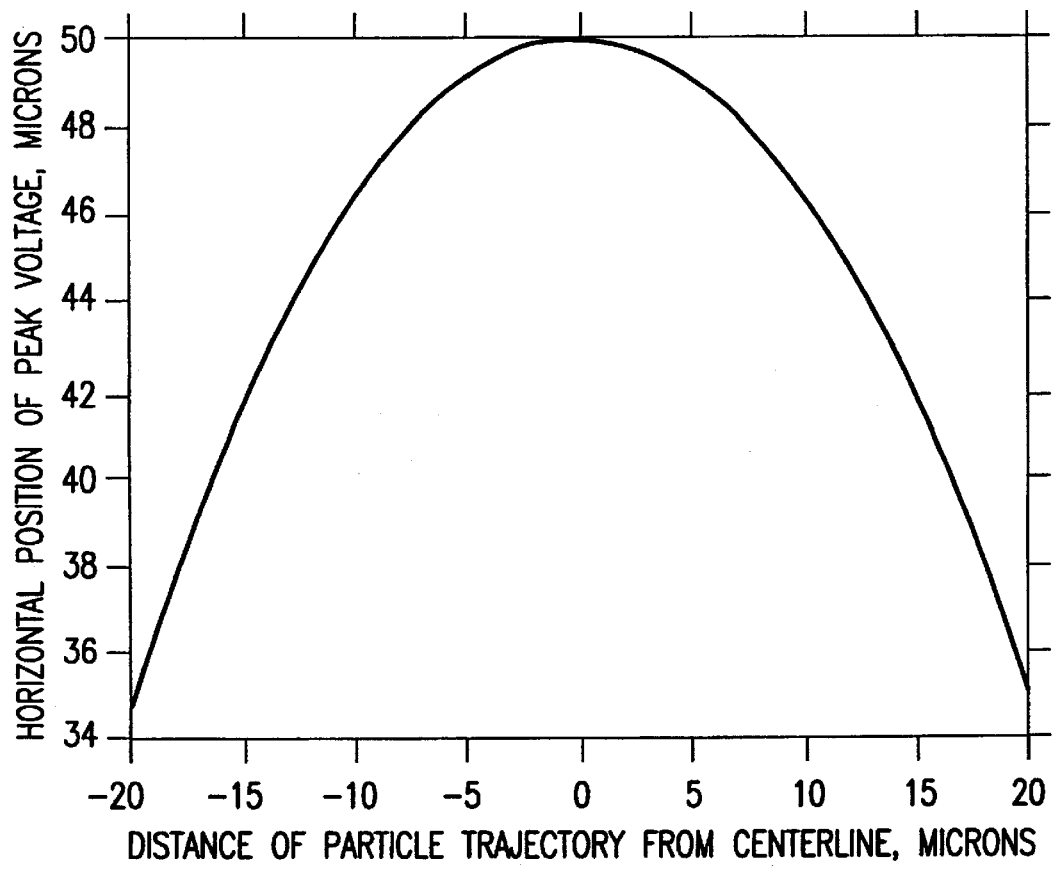
FIG. 17 is a finite element simulation, according to embodiments of the present disclosure. The curve is an approximation for a channel geometry based on a hyperbolic cosine function.

The finite element simulations of FIG. 17 show that the position, in the horizontal direction, from the center of the sensor at which the peak voltage perturbations to the sensor electrode occur depends on how far the particle trajectory is away from the horizontal centerline of the channel. One peak occurs as the particle travels through the first dielectric membrane and a second peak, of opposite sign, occurs as it travels through the second dielectric membrane before leaving the sensor. The curve shown in FIG. 17 is an approximation for the channel geometry shown earlier based on a hyperbolic cosine function. Finite element or other analysis methods may be used to obtain characteristics for any channel geometry, based on the procedures provided herein combined with what is understood in the art of, for instance, fluid dynamics.

Figure 18:
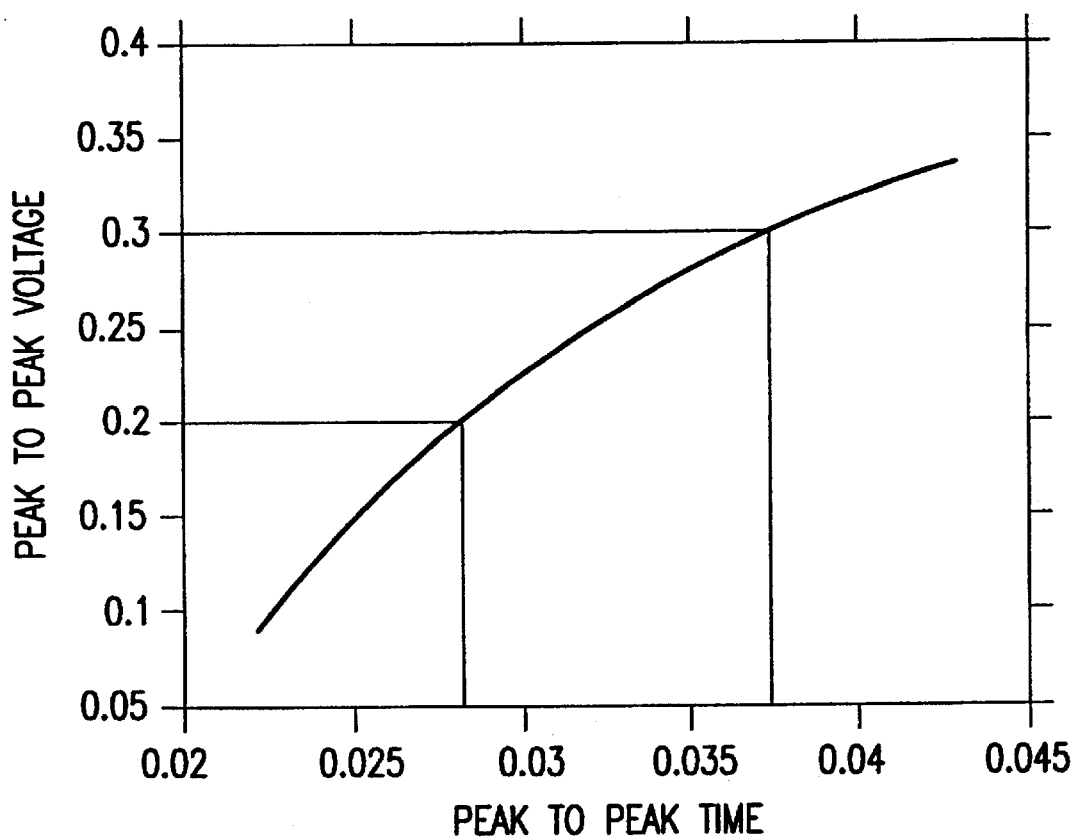
FIG. 18 is a plot showing peak to peak voltage for a 10 $\mu$m particle travelling through an impedance sensor channel as a function of the time it takes to travel from the first peak position to the second of opposite sign, according to embodiments of the present disclosure.

Peak to peak voltage for a 10 μm particle travelling through an impedance sensor channel can be described as a function of the time it takes the particle to travel from the first peak position to the second of opposite sign (FIG. 18). This curve was calculated from the characteristics shown in FIGS. 11–17 and takes into account the relationships between peak positions, peak heights, fluid flow velocity and a distance of the particle trajectory from the horizontal centerline of the sensor. It shows that a 10 μm particle that has a peak to peak time of 0.028 seconds and causes a peak to peak sensor voltage perturbation of 0.2 volts is identical to a 10 μm particle having a peak to peak time of 0.037 seconds that gives a peak to peak voltage perturbation of 0.03 volts. By measuring the peak to peak times for different particles and then using a characteristic curve like this one constructed for the sensor geometry being used, sensor voltages can be corrected to provide accurate impedance data for all particles regardless of their trajectory through the sensor channel.

Figure 19:
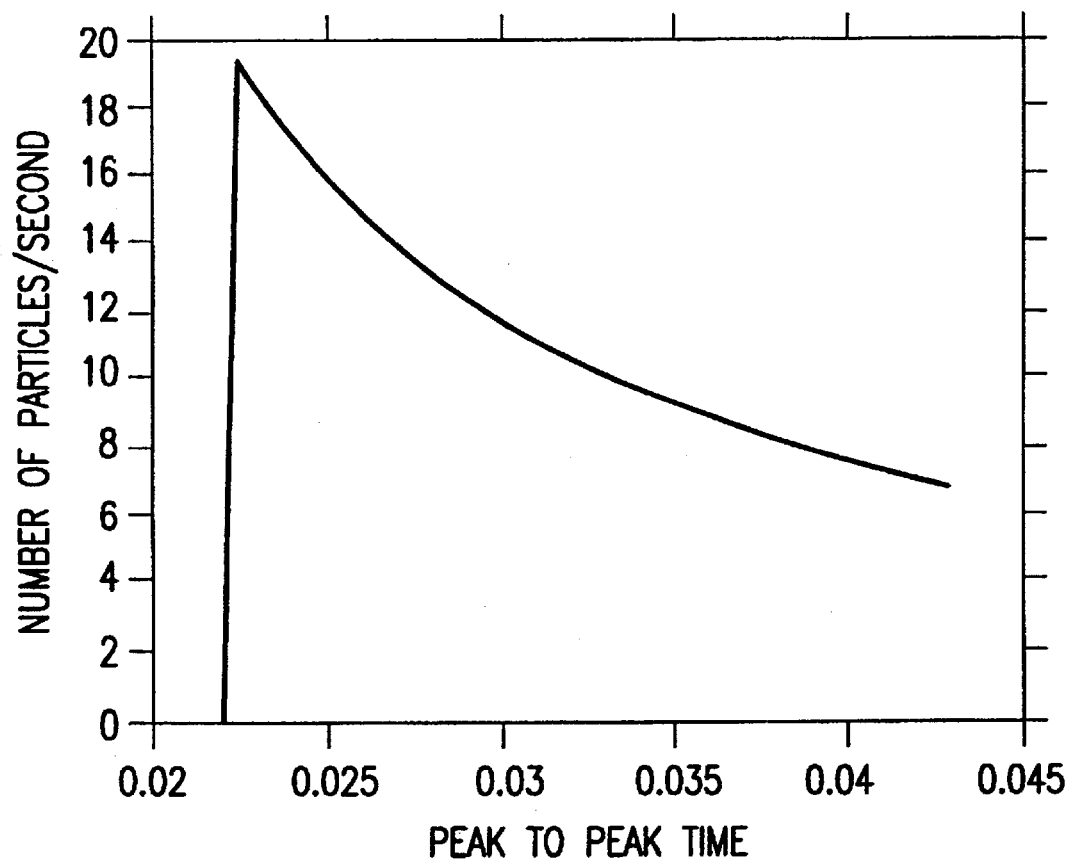
FIG. 19 is a plot showing the number of particles passing through a sensor channel as a function of their peak to peak time, according to embodiments of the present disclosure.

During the analysis of a sample using the impedance sensor, a count of the number of particles passing through the sensor channel as a function of their peak to peak time may be determined from the sensor voltage data, and a profile like the one above can be plotted. The curve in FIG. 19 reflects the distribution of particle velocities that results from the flow profile in the sensor channel. The shortest transit time observed corresponds to the maximum flow velocity, which occurs for particles being carried along the centerline of the channel. The profile may therefore be used to calculate the flow rate in the channel and, knowing the total number of particles counted in a given period of time, this information may be used to calculate the concentration of particles present within the sample. In this way, the concentration of particles in the sample may be determined from the impedance sensor signals without using ancillary methods to measure the volume of sample suspension that flows through the channel. This represents a major improvement over conventional electrozone sensors that rely on sophisticated fluid control and metering apparatus to allow them to determine particle concentrations. Its freedom from such metering equipment makes sensors disclosed herein simpler and more flexible than previous designs.

Alternating Current Excitation

Figure 20A:
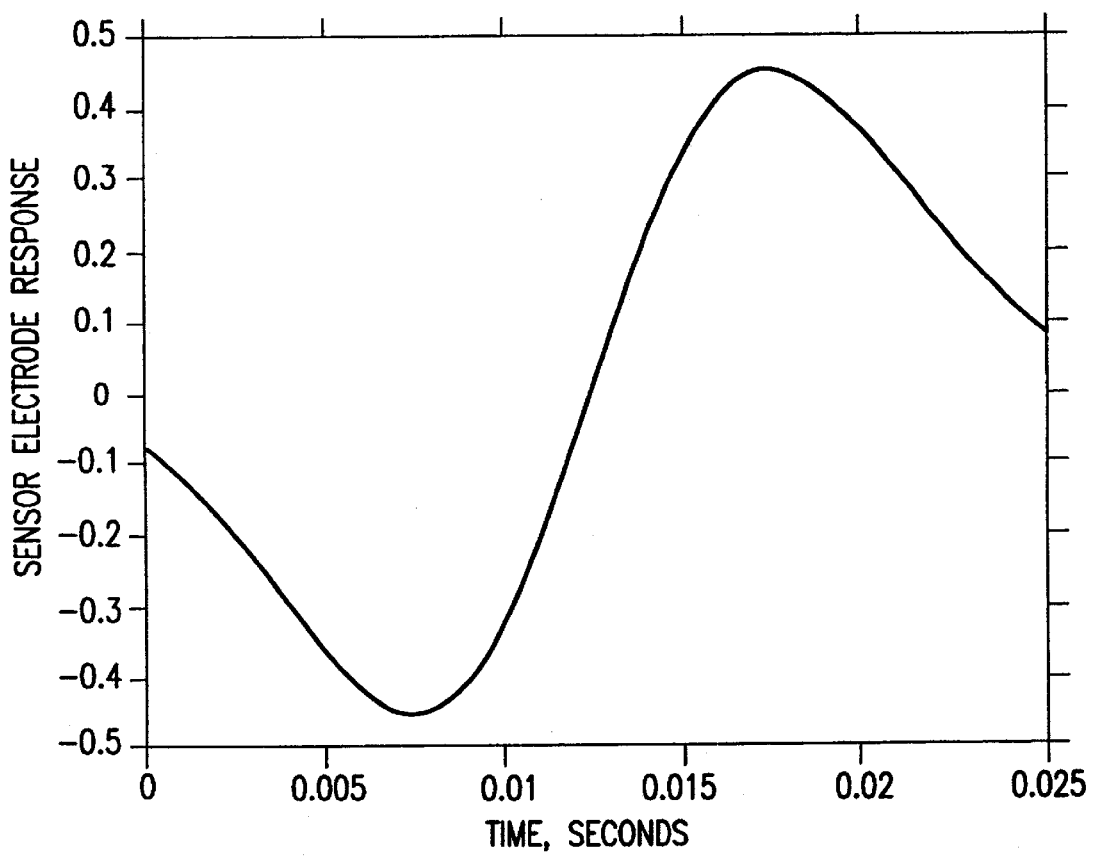
Figure 20C:
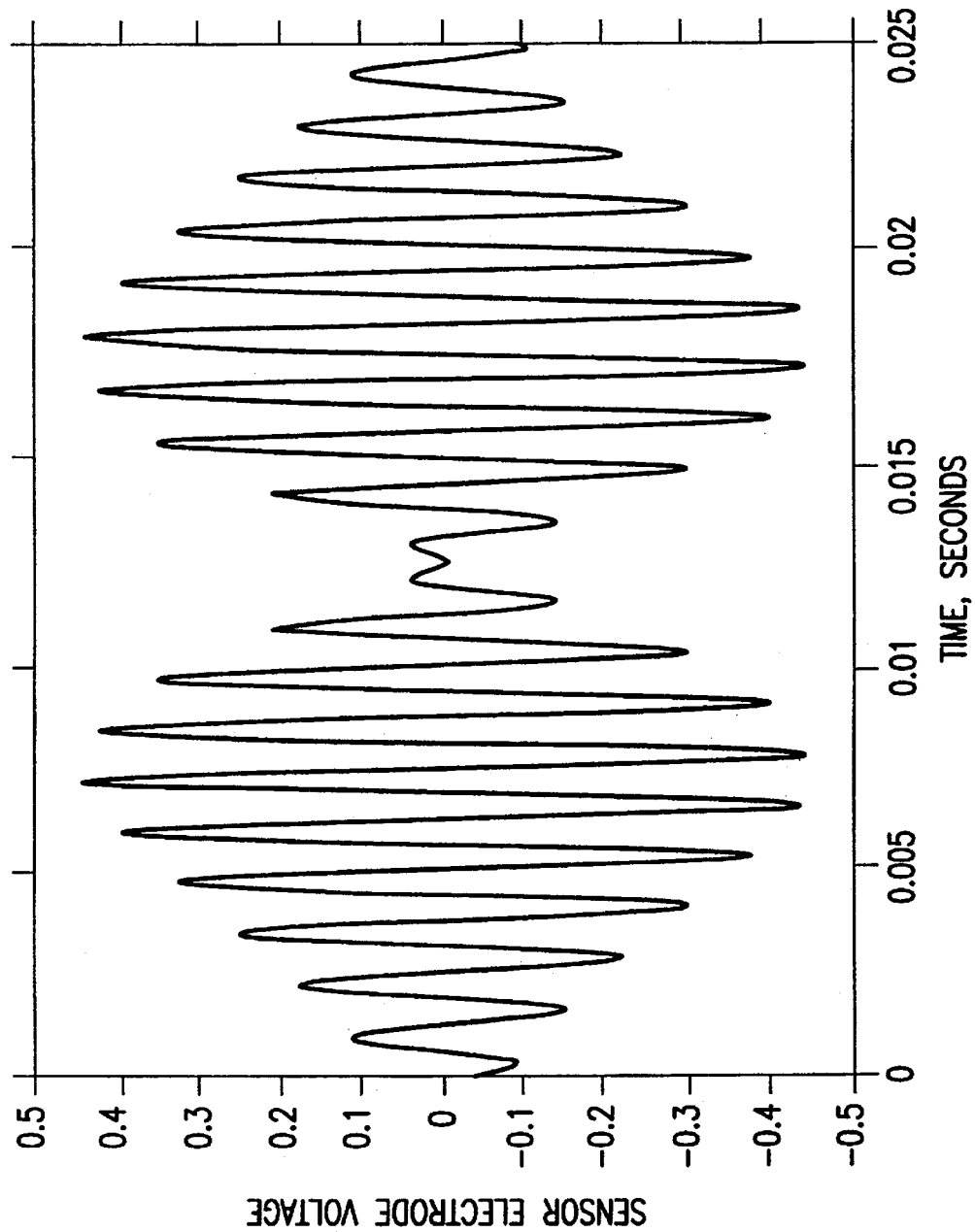

Direct Current (DC) methods, used in the original Coulter Counter and other standard impedance sensors, are augmented by Alternating Current (AC) approaches in which the electrical current that is passes through the channel contains not only a DC current but also an AC current. Through this enhancement, dielectric information about the particles can also be deduced, adding greater discriminatory capabilities to the method. When AC voltages are used for excitation, the signal appearing on the sensor electrode is an AC voltage whose magnitude and the phase is modulated as the particle passes through the sensor channel. The phase and strength of the sensor signal reflect the particle response (FIG. 20A) times the AC signal (as in the example, a single frequency sine function, FIG. 20B). The resulting sensor signal is shown in FIG. 20C. Note that the particle response reflects the effective impedance at the AC frequency. In general, the particle response is frequency dependent and the frequency dependency can be used to characterize or identify the particle. To detect the particle properties, the sensor signal may be multiplied by the excitation waveform or one of its components, and the resulting signal may be passed through a low pass filter to recover the particle response shown in FIG. 20A. Such packet detection may be accomplished by analog methods or by digital signal processing using, for example, a DSP or FPGA chip as is known in the art.

Figure 21:
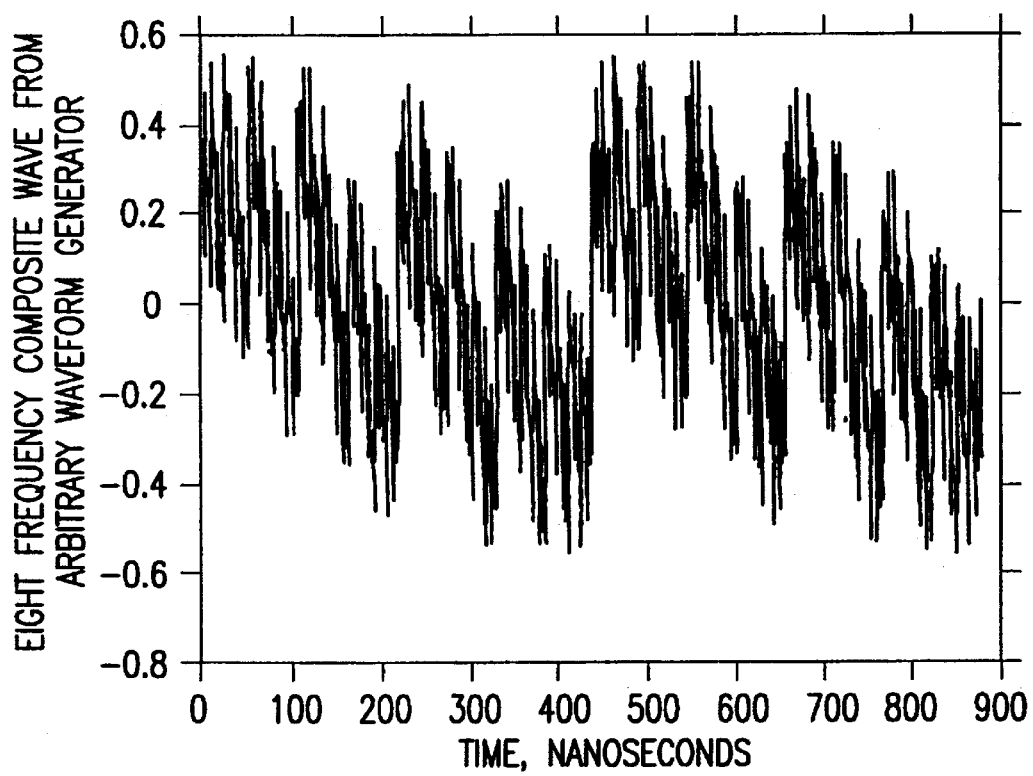
FIG. 21 is a plot showing a waveform containing eight different frequencies spanning a range of 128:1, according to embodiments of the present disclosure.

In order to provide sufficient information to fully characterize the dielectric properties of a particle, it may be desirable to use excitation signals composed of multiple frequency components. For example, the waveform shown in FIG. 21 contains eight different frequencies spanning a range of 128:1. Other excitation signals may contain 2, 3, 4, 5, 6, 7, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more different frequencies. The frequencies may be multiples of a base frequency (i.e., the base frequency multiplied by 2, 4, 8, 16, 32, 64 and 128) or have a more random relationship. The impedance sensor response will also contain a contribution from each of the frequency components of the excitation signal, but each component will be modified in accordance with the particle's dielectric response characteristics at that frequency.

Sensor Replacement

One problem with many sensors and components in microfluidic systems is the need for rigorous cleaning or replacement of various elements due to unwanted accumulation within the element. For any system using small diameter tubes or channels, keeping the system clean can be problematic. Small amounts of material can effectively block a passageway and cause device function to drastically decrease. Many systems have elaborate cleaning protocols, manual or automated, that take substantial time and reagents. However, even with an optimized cleaning protocol, it is often still difficult to obtain a clean system. It is often preferred to use disposable elements and provide a clean substrate for every use. Impedance sensors of the current disclosure are designed such that they facilitate rapid and potentially automated replacement of the sensor element to overcome blockage and cleaning issues.

The current system permits the rapid exchange of sensor elements. The sensor element may be changed manually or automatically and may be changed between experiments or during experiments when flow through the sensor channel has been halted. These sensor elements can have different channel characteristics such as shape and size which allow the sensor characteristics to be optimized on the fly to match the needs of different particle sensing needs. For example, a sensor element, or composite membrane sensor assembly containing a sensor electrode sandwiched between two dielectric membranes may be removed from a flow system and replaced with another sensor or composite membrane sensor assembly with a different size or shaped hole to create a sensor element with a more or less constricting fluid flow path. When the particles to be analyzed have a substantially different particle size distribution from the previous sample, this exchange of sensor elements may be advantageous.

Impedance Signal Processing I

Once a signal from the sensor has been corrected to take into account trajectory through the sensor channel using sensor channel characteristics such as those described herein, and processing by detector electronics is completed, the resulting data are the in-phase and out-of-phase components of the particle impedance perturbation at each of the frequencies that were present in the excitation signal. Each of these impedance parameters will contain unwanted contributions from thermal noise as is well known in the art of electronics. However, the impedance properties of particles in the frequency range between 1 kHz and 1 GHz are dispersive rather than resonant in nature. This means that both the in-phase and out-of-phase impedance data obtained for particles by the impedance sensor must be functions of frequency that are smooth and members of a limited set of allowed curves. Furthermore, the Kramers-Kronig equation (Kramers, H. A., Nature, 117 (1926) 775, Kronig, R. de L., J. Opt. Soc. Am. 12 (1926) 547), is well known in the art of dielectrics and provides an explicit relationship between the in-phase and out-of-phase curves that cannot be violated. By fitting smooth curves from the set of curves characteristic of dispersive dielectric responses to the in-phase and out-of-phase impedance data points at the different frequencies contained in the excitation signal, and by further constraining the in-phase and out-of-phase curves so that they obey the Kramers-Kronig relationship, the quality of the impedance data for particles passing through the sensor can be greatly improved so as to increase the effective signal to noise ratio of the impedance measurements.

Furthermore, if the particle types being measured are known to have dielectric properties that are limited in some other way, the analysis may be further constrained so as to include an appropriate mathematical model for the particle dielectric characteristics. For example, many mammalian cells have dielectric characteristics that are described well by a single-shell dielectric model. By constraining the curve fits of the dielectric data from the impedance sensor to fit this model, explicit data reflecting the structure of the cells under measurement may be derived. All of these data analysis steps may be accomplished in a computer using appropriate algorithms or in dedicated DSP or FPGA hardware programmed for this purpose or in a combination of these means. The data analysis techniques employed may be single-pass least squares methods or iterative error minimization methods, as are well known in the art of data processing, or a combination of these but need not be limited to these methods.

The sensor signal containing multiple frequencies may be parallel-processed by multiplying it by each of the frequency components of the original excitation followed by low pass filtering (product detection). In this way, the effective impedance of the particle at each of the frequencies may be independently derived from the sensor signal even though the excitation electrodes applied them simultaneously as a single, composite signal. This may be accomplished by digital signal processing using a DSP or FPGA chip as known in the art.

After signal processing and impedance analysis, data for individual particles, for groups of particles, and statistical data for populations of particles may be provided. Processed data of this kind or individual particle data may be used for particle analysis, identification, or classification. Such data may in turn allow conclusions to be drawn by those skilled in the art. For example, population distributions of impedance properties of cells allow cell type, size, viability, apoptotic state, and membrane and cytoplasmic status to be drawn by life scientists skilled in the art and allow blood cell subpopulation differential analyses to be performed. With the benefit of this disclosure, those of ordinary skill in the art will recognize a host of other potential applications.

Impedance Signal Processing II

In one embodiment, the waveform that is used to drive the electrodes on either side of the impedance sensor membrane is synthesized by a field programmable gate array (FPGA, model Altera FLEX EPF10k200SBC600-1). An exemplary waveform (FIG. 21) consists of a composite of 8 separate sine waves having frequencies f, 2f, 4f, 8f, 16f, 32f, 64f, and 128f. The fundamental frequency f is adjustable and typically about 10 kHz. The FPGA generates this composite signal in the form of a string of digital numbers that are converted to a voltage signal by appropriate equipment such as a Burr Brown DAC902U digital to analog converter. An output stage drives the electrodes on either side of the sensor membrane, one with this drive signal and the other with a signal of the opposite phase. The signals driving the driver electrodes, including a signal and a signal of opposite phase, are referred to generically as the "drive signal." Other methods and other electronic components known in the art may be used to produce waveforms, which may be of any desired composition with respect to Fourier components, and to drive the sensor. Other approaches to producing waveforms and driving electrodes with voltage signals are well known in the art.

In one embodiment, a low noise preamplifier located very close to the sensor amplifies the signal from the center metal layer of the sensor membrane. The resulting higher amplitude signal, which incorporates the desired impedance information, may be fed to a circuit based on an Analog Devices AD9224 12 bit analog to digital converter (DAC). The inventors call the signal from the sensor membrane the "impedance signal." The digital output from this circuit may be fed to a second Altera FLEX FPGA. The rate of sampling of the impedance signal provides 16-fold oversampling, adding three extra bits of resolution beyond the 12 bit width of the digital to analog converter by a mechanism well known in the art.

In this embodiment, the second FPGA accomplishes a Fourier-type analysis of the impedance signal to derive from it the intensities of the in-phase and out-of-phase components of the same frequencies used to compose the drive signal. These impedance signal frequency components are represented as 24 bit words that are passed to a digital signal processor (DSP) board, which may be based on a Texas Instruments TM S320 C6211 integrated circuit. At this stage, the impedance data is represented by a stream of 16,000 digital samples per second, each comprising sixteen 24 bit words: one 24 bit word for each real and imaginary component for each of the 8 frequencies. The inventors refer to these sixteen data sets as the "data channels." There are two data channels for each of the 8 frequencies; one is the in-phase component, the other the out-of-phase component.

The function of the DSP is to analyze this data stream from the impedance data to detect changes in the data that correspond to particles passing through the impedance sensor. The inventors call these changes "particle events." Exemplary shapes of impedance signals corresponding to a particle event has been shown earlier in this disclosure. Because of the rapid sampling of the impedance data, a single particle event, which may typically last from 1 to 5 milliseconds as the particle passes through the sensor, corresponds to between 16 and 80 digital samples, each comprising sixteen 24 bit words (one 24 bit word for each real and imaginary component for each of the 8 frequencies). The signals may contain significant electrical noise especially if the impedance signal preamplifier is set to high gain in order to detect small particles producing small impedance signals. As is well known in the art, it is advantageous to filter signals to reduce the noise as much as possible. In one embodiment, the first step of filtering is to apply low pass digital filtering of the signals by computing the moving sum of N digital samples where N is of the order of half the number of digital samples corresponding to a particle event (i.e. typically between 8 and 40).

The changes in the digital data that occur with time during a particle event are typically of different intensities and of different phases for each of the sixteen data channels. By using an algorithm that is independent of phase to correlate the time changes in the 16 channels, a robust way of detecting particle events is produced.

In one embodiment, an algorithm in the DSP is used to derive a composite signal comprising the moving sum of the (unsigned) magnitudes of changes with time in each of the sixteen digital channels. This sum is conducted over $N_1$ digital samples, where $N_1$ is typically of the order of half the number of digital samples within a particle event. This produces a signal related to the average square root of the power density of changes summed for all sixteen channels. This signal has a mean value that reflects the mean noise (the "noise floor") and increases when a particle event occurs. In one embodiment, a particle event is detected by determining when this signal exceeds a given threshold value above the noise floor. This threshold value may be adjusted to alter the sensitivity of the system to different particle sizes.

Once a particle event is detected, portions of the signal about the particle event are analyzed. In one embodiment, all 16 channels of $N_3$ digital data samples preceding, and $N_4$ digital data samples following, the point at which the threshold was exceeded are saved by the DSP for further analysis. Such additional analysis may be undertaken by the DSP itself, by an additional DSP or microcomputer, or by a host computer after uploading the $(N_3+N_4)$ samples. $N_3$ and $N_4$ are chosen to be sufficiently large that the saved data covers the entire particle event, i.e. includes the entire data record of the impedance signal as the particle enters, passes through, and leaves the impedance sensor. For example, if particle events span up to 80 samples in a given experiment, 100 samples might be saved spanning the range from 50 points before the peak to 50 points after. After saving the digital samples for a particle event, the DSP continues to analyze the digital sample stream looking for additional particle events. In this way, the impedance data is continuously screened for particle events, and the data for these alone are saved for further analysis.

The moving sum of the magnitude of the signal changes of the 16 channels of a saved particle event has a peak whose position indicates when a particle has passed half way through the impedance sensor. The width of the peak at half its height above the noise floor is proportional to the amount of time the particle took to travel through the sensor. In one embodiment, the velocity of each particle is calculated from saved event data by dividing the length of the sensor by the time the particle takes to transit the sensor as inferred from the peak width. Particles travel at different velocities according to how far they pass from the axis of the sensor. By taking the average of the velocities for many particles, the mean fluid velocity may be deduced. Multiplication of this mean flow velocity by the area of the sensor orifice allows the mean fluid flow rate to be deduced. Division of the mean number of particles counted per unit time by the mean flow rate gives the concentration of particles in the sample.

In one embodiment, the saved particle event data is further analyzed to deduce size, dielectric, and conductivity data for each particle. As shown earlier from computer simulations, the shape of the impedance sensor signal corresponding to a particle event depends on the axial displacement of the particle transit path from the center of the sensor. When highly accurate particle data is needed, this axial displacement can be taken into account. It is possible to calculate the displacement position from the particle velocity and mean fluid velocity data (deduced using the method described above) because, as is known in the art, fluid flowing under laminar flow conditions within a flow path follows a parabolic flow profile. If the velocity calculated for a given particle is $v_p$ and the mean fluid flow velocity based on the average of the velocities of many particles is $v_m$ then the relative displacement x/r at which the particle traversed the sensor from its central axis, assuming that the impedance sensor has an orifice radius r, is described by the following equation:

$$\frac{x}{r} = \left(1 - \frac{2v_p}{3v_m}\right)^{\frac{1}{2}}$$

for a parabolic flow profile. The family of impedance sensor response characteristics $S(l, x/r)$ representing the impedance signals as a function of distance l along a particle transit path for axial displacements $x/r$ may be stored in a lookup table in one embodiment of the impedance signal analysis system. Alternatively, in another embodiment, these characteristics may be calculated from an empirical equation. Each characteristic curve is normalized so that its integral along a path L that spans the entire length of a particle transit from the point where it enters the sensor to the point where it leaves obeys the expression:

$$\int_{-L/2}^{L/2} S\left(l, \frac{x}{r}\right) \cdot \hat{S}\left(l, \frac{x}{r}\right) \cdot dl = 1.$$

Here, l is the distance of the particle from the center of its transit through the sensor, $\hat{S}(l,x/r)$ is the true strength of the impedance signal for a standard particle along the particle transit path, and $S(l,x/r)$ has the same form as $\hat{S}(l,x/r)$ but is scaled to ensure normalization according to the integral expression. As shown earlier, the shape characteristics of the impedance signals are antisymmetric about the mid point of the transit path, so that $$\int_{-L/2}^{L/2} S\left(l, \frac{x}{r}\right) \cdot dl = 0.$$

Because of these properties, the intensity coefficients $A_i$ of the sixteen impedance signals $C_i$ comprising the real and imaginary parts of the eight frequencies (embodied in the saved impedance signal sample) may be obtained by calculating the overlap integral for each channel in turn with the relevant shape characteristic $$A_i = B_i \int_{-L/2}^{L/2} C_i(l) \cdot S\left(l, \frac{x}{r}\right) \cdot dl$$

where the constants $B_i$ correct for gain imperfections in the electronics of the 16 channels. The 16 $A_i$ coefficients summarize the frequency and phase characteristics of the perturbation caused by the particle to the overall impedance of the sensor channel. Besides using this overlap integration technique, it will be understood that one could also use other well-known signal processing approaches such as, but not limited to, (a) calculating a correlation function or autocorrelation function or (b) performing a double integral of the signal. Although the double integral technique may be more noise prone, it would nevertheless work well for good signal to noise ratios.

Other approaches to solving this problem may be derived from digital signal processing methods known in the art. Therefore, the algorithm described above is an example of a specific embodiment only.

Figure 22:
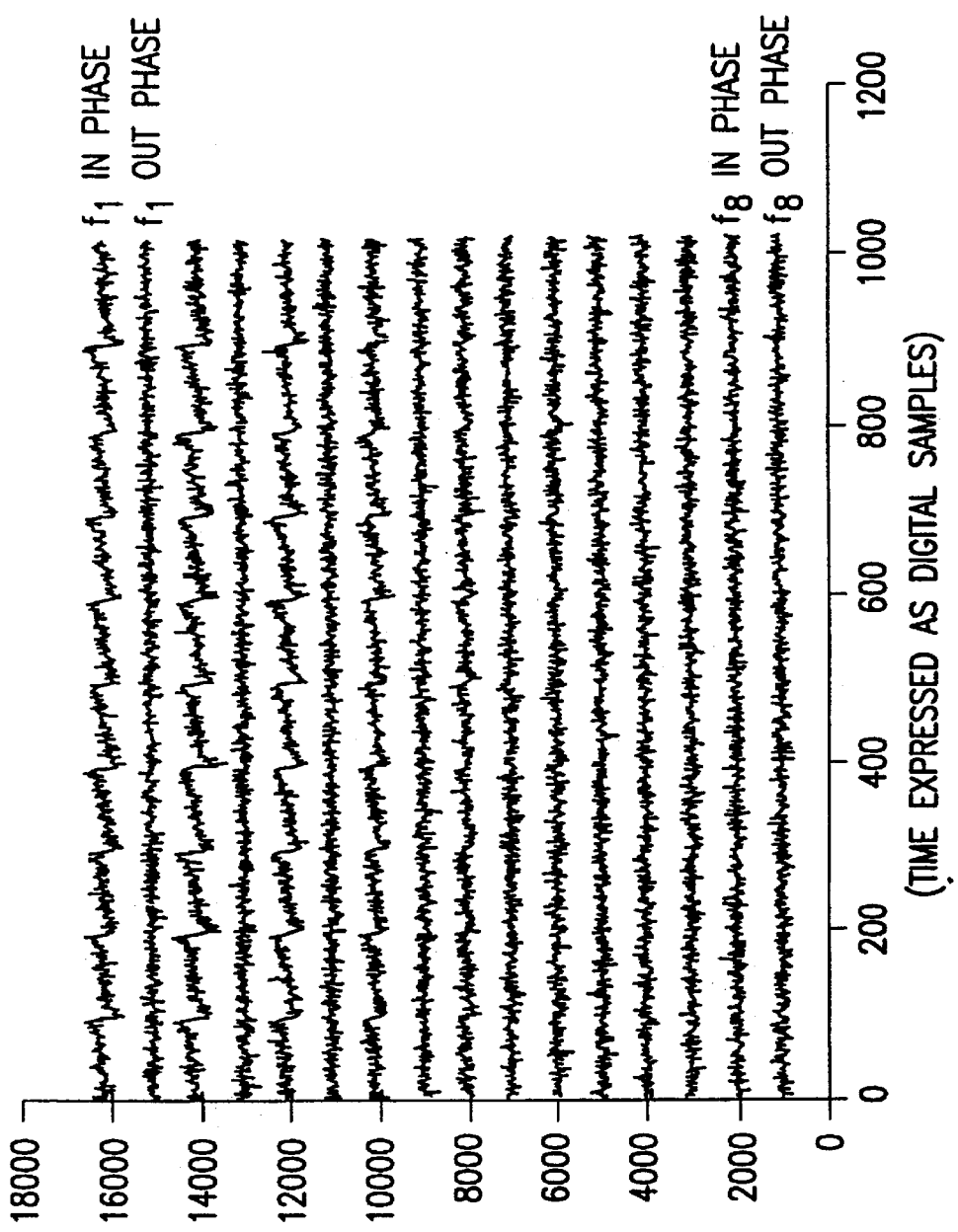
FIGS. 22–30 illustrate simulation data taken in accordance with specific embodiments of data processing aspects of the present disclosure.

FIGS. 22–30 illustrate simulation data taken in accordance with specific embodiments of data processing aspects of the present disclosure. In FIG. 22, there is shown simulated impedance signals for a train of 9 particles passing through a sensor. Included is simulated Gaussian noise. The sixteen separate signals represent the real and imaginary components for each of eight frequencies, as illustrated.

Figure 23:
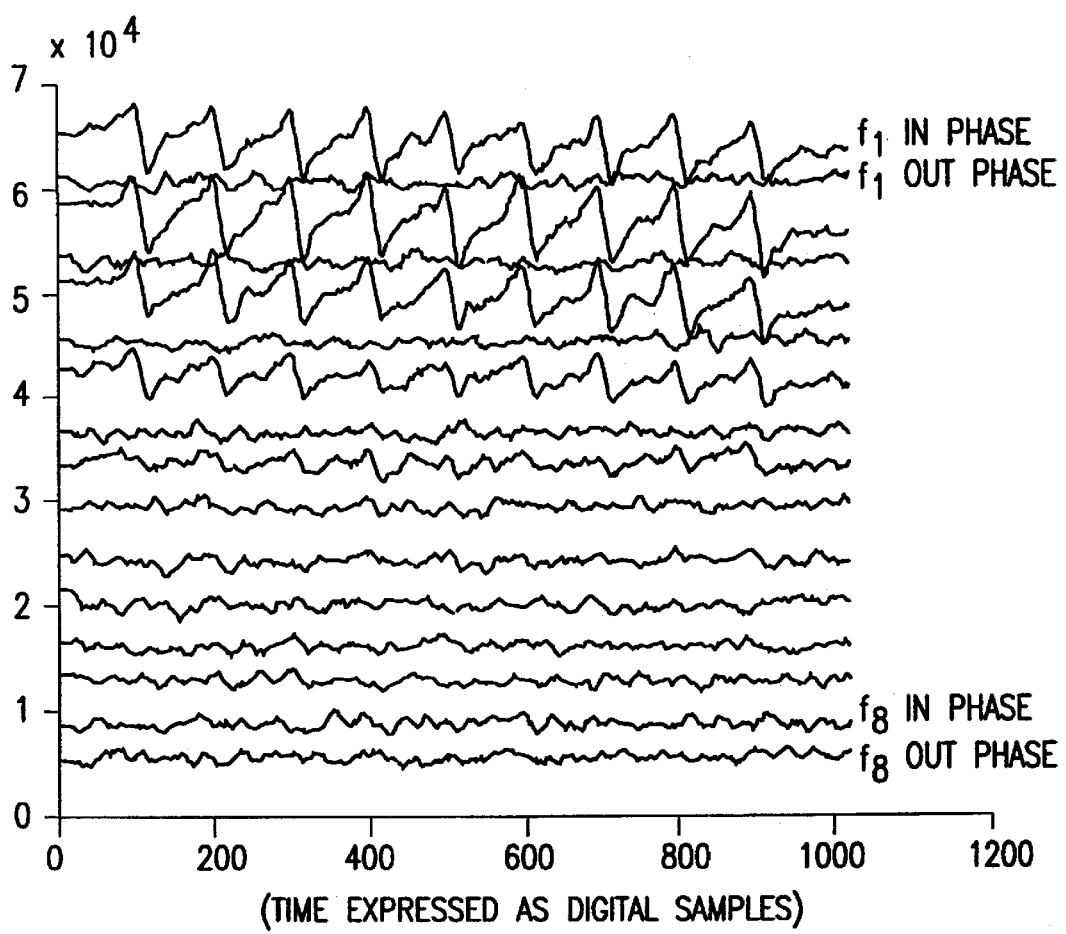

FIG. 23 shows the data of FIG. 22 after applying a low pass filter—here, a moving sum of 16 digital samples.

Figures 24, 25:
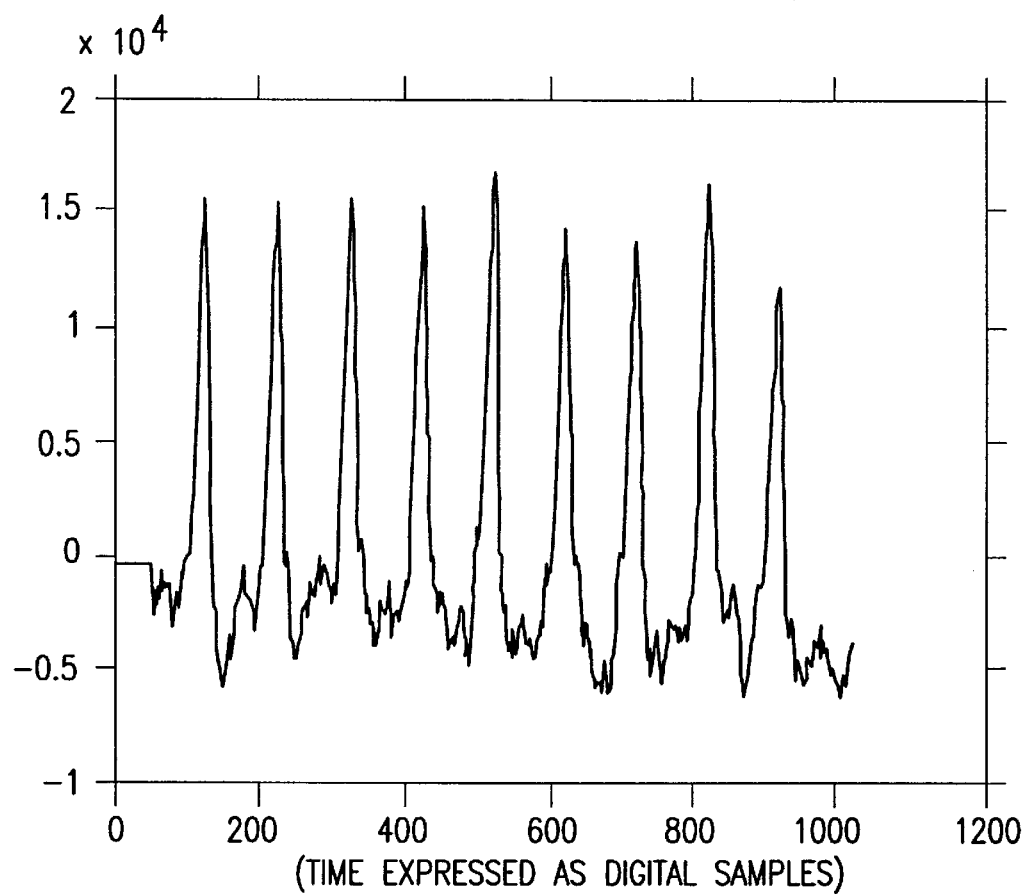

FIG. 24 shows the signal derived by computing the moving sum of absolute differences over 16 digital samples summed over both real and imaginary components for all 8 frequencies (i.e., it shows computing the power in each channel and then adding all channels). The mean signal level has been subtracted to remove a noise floor.

FIG. 25 is a table showing peaks detected from the signal of FIG. 24 by thresholding. As shown, the columns of the table include, from left to right: peak start time (seconds), peak end time (seconds), and peak height.

Figure 26:
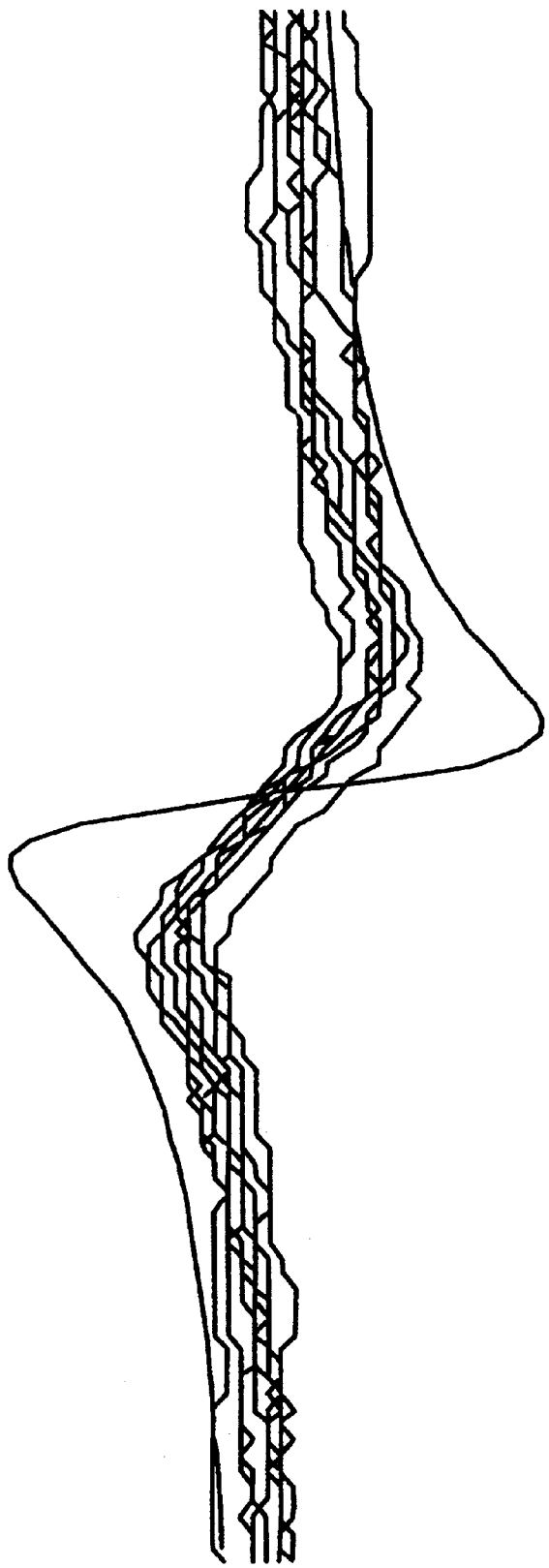

FIG. 26 shows a comparison of a theoretical signal (single smooth curve) and the signals extracted from the digital sample for the in phase components at $f_1$ for the 9 particles in the simulation.

Figure 27:
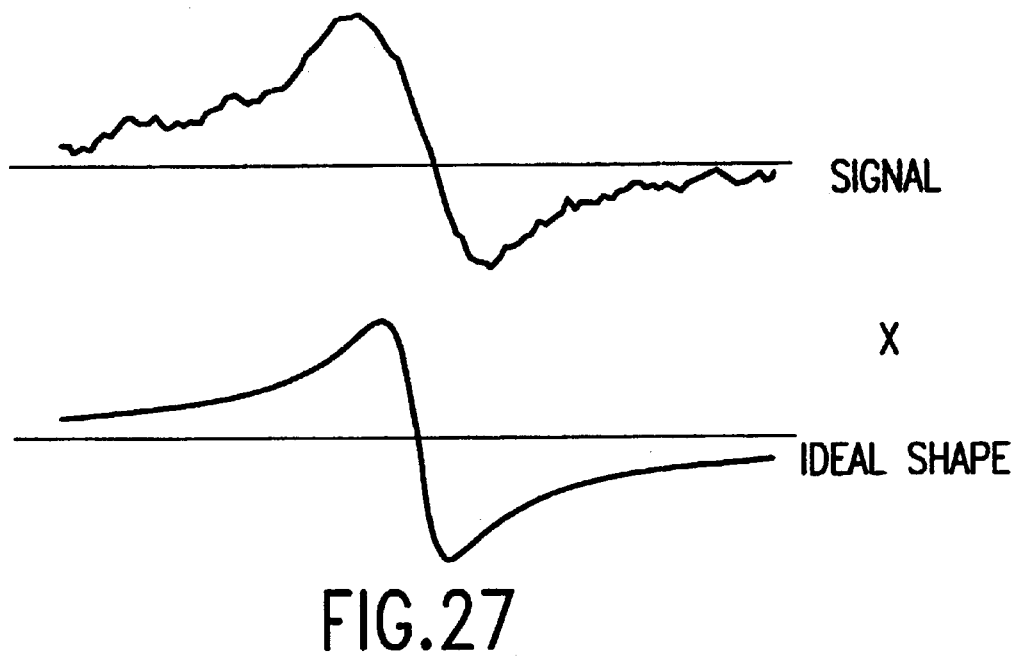
Figure 28:
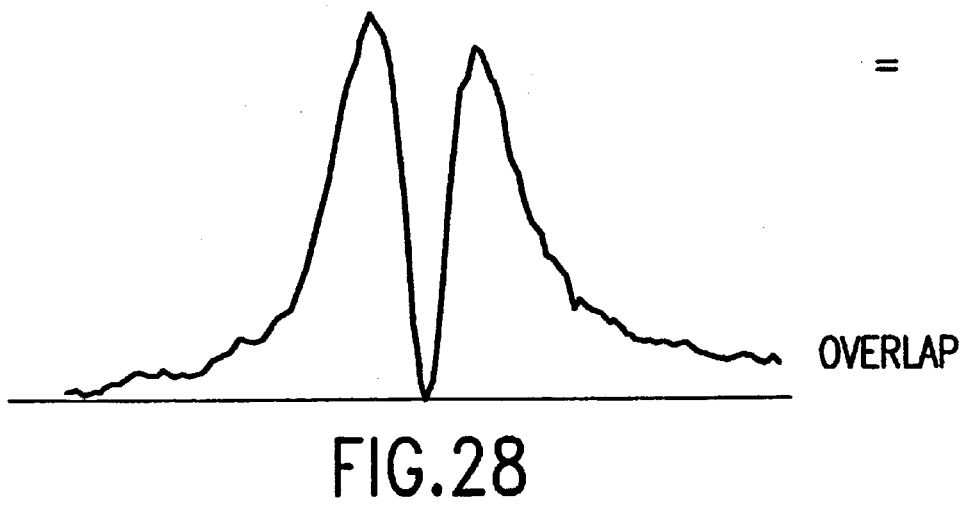

FIG. 27 illustrates the multiplication of the signal from one of the data channels with the theoretical signal shape. FIG. 28 shows the area of this multiplication, which reflects the intensity of the impedance signal.

Figure 29:
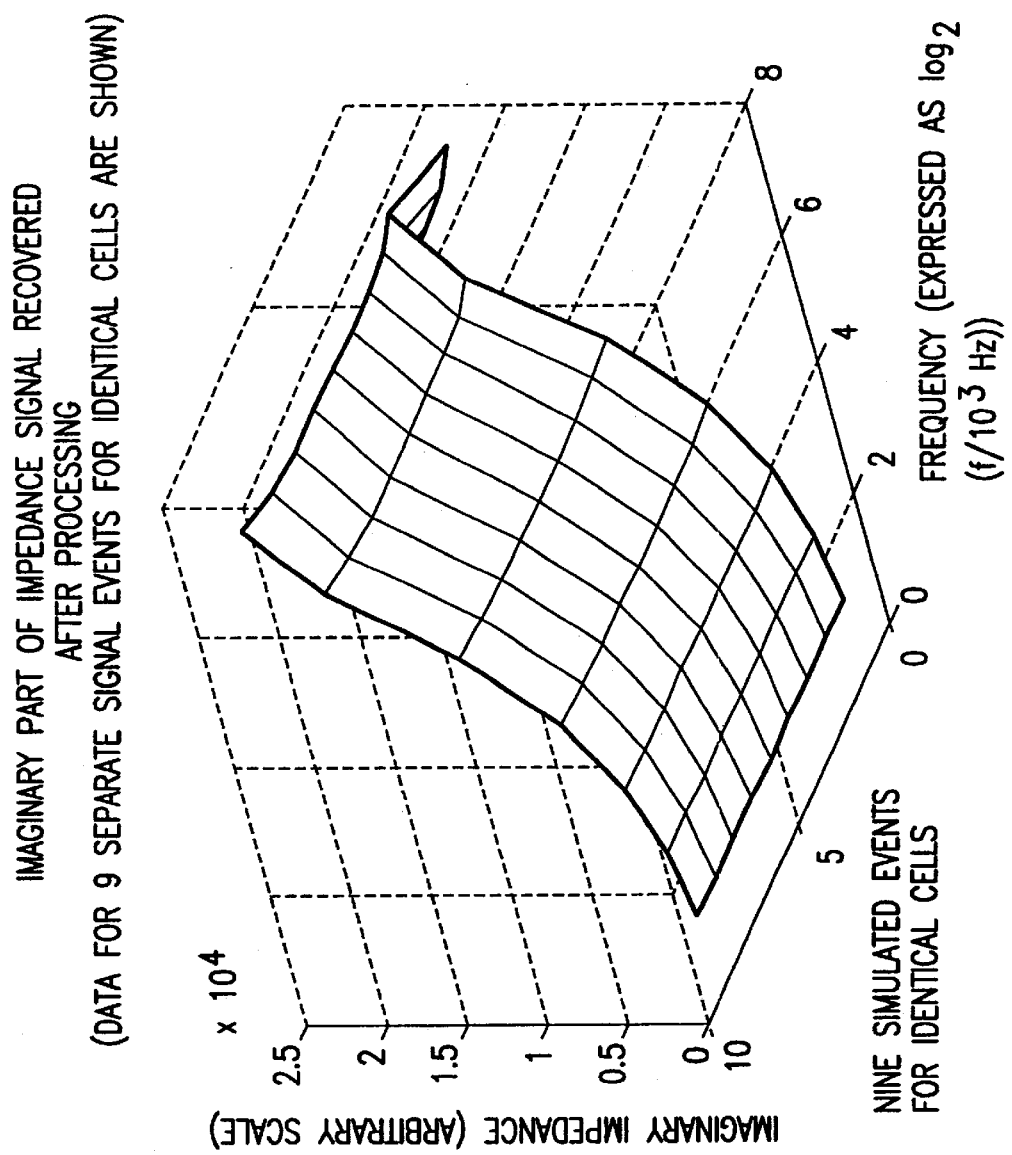
Figure 30:
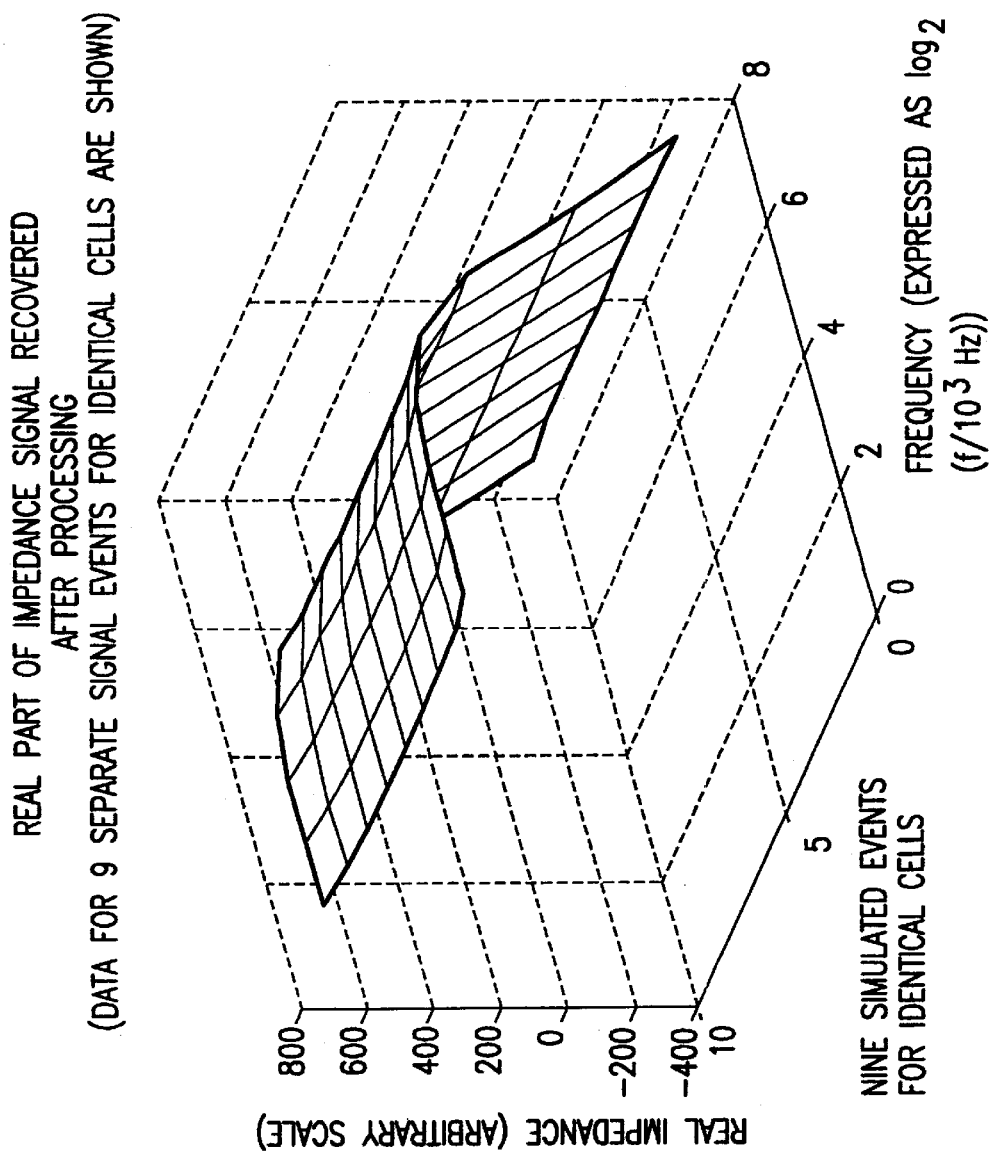

FIGS. 29 and 30 respectively show the imaginary and real parts of impedance signal recovered after processing. These plots show data for 9 separate signal events for identical cells.

Impedance Data

Although the impedance perturbation information is of interest, a more useful parameter in many applications is the impedance data for the individual particles themselves. In one embodiment, additional analysis to the coefficients $A_i$ is employed so as to extract the explicit particle impedance information. To accomplish this, it is first noted that the odd-indexed coefficients $A_1, A_3, A_5 \ldots A_{15}$ are proportional to the in-phase, or resistive, components of the impedance perturbation for the eight frequencies while the even coefficients are proportional to the corresponding out-of-phase, or capacitative, components. In this analysis it is assumed that the out-of-phase part of the particle impedance arises from particle capacitance and not inductance. Inductive impedances will correspond to negative capacitance values.

Figure 31:
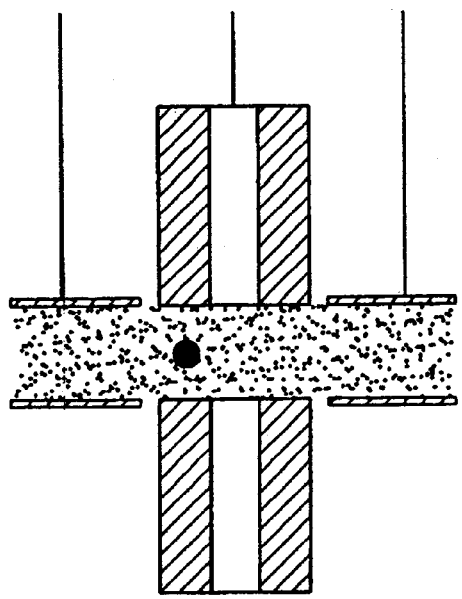
FIG. 31 shows an impedance sensor embodiment according to the present disclosure.
Figure 32:
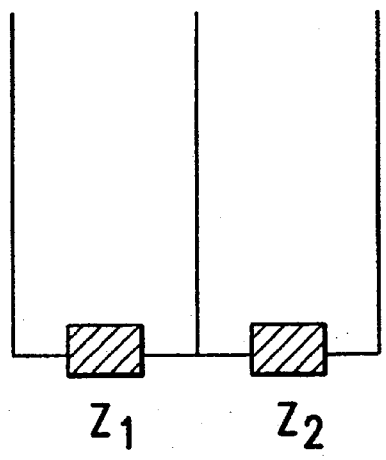
FIG. 32 is an illustration of the effective impedance circuit of FIG. 31.

The impedance sensor embodiment of FIG. 31 has an effective impedance circuit as shown in FIG. 32. Assuming that the impedances are driven by a symmetrical voltage source with voltage waveforms V and −V, the voltage at the junction of the impedances will be given by $$\frac{\Delta V}{V} = \frac{(Z_1 - Z_2)}{(Z_1 + Z_2)}.$$

In the absence of a particle, $Z_1 = Z_2$ and the output signal is zero. Expressed in terms of conductivities, $K_1$ and $K_2$ where $K_1 = 1/Z_1$ and $K_2 = 1/Z_2$, the junction voltage is given by $$\frac{\Delta V}{V} = \frac{(K_2 - K_1)}{(K_1 + K_2)}.$$

In many applications, such as the characterization of cells, for example, the particle size is very small compared to the sensor volume (e.g., 1% or less). In such cases, the denominator may be approximated as $2K_1$ and assumed to be constant so that the voltage perturbation when a particle is present can be accurately approximated by $Q(K_2 - K_1)$ where Q is a calibration constant for the measurement. The conductivies $K_1$ and $K_2$ can be expressed in terms of the geometrical characteristics of the sensor and the complex permittivity of the fluid inside the sensor in the form:

$$K = \varepsilon^*_{sensorfluid} \frac{A_{orifice}}{L_{orifice}}$$

where $A_{orifice}$ and $L_{orifice}$ are the effective area of the membrane sensor channel and the electrical distance from where the particle enters the sensor to the sensor's midpoint, respectively. The complex permittivity of the fluid inside the sensor includes any contribution from the particle and can be written:

$$\varepsilon^*_{sensorfluid} = \varepsilon_{sensorfluid} - j\sigma_{sensorfluid}/\omega$$

where $\varepsilon_{sensorfluid}$ is the real permittivity ("dielectric constant") of the fluid, $\sigma_{sensorfluid}$ is the conductivity of the fluid, and $\omega = 2\pi f$ is the angular frequency of a voltage component of V that is under consideration, and $j = (-1)^{1/2}$. When V is a composite of many frequencies, the signal from the sensor will be the sum of a voltage for each frequency each bearing similar dependences.

Because $A_{orifice}$ and $L_{orifice}$ are the same for both impedances in the sensor, the voltage signal corresponding to a particle can be further simplified to $\hat{Q}(\varepsilon^*_{sensorfluidnoparticle} - \varepsilon^*_{sensorfluidwithparticle}) = \hat{Q}\Delta\varepsilon^*_{sensor}$. This complex number contains both the in phase (real) and out-of-phase (imaginary) components of the signal. In the embodiment described here, each data sample comprises one $\Delta\varepsilon^*_{sensor}$ for each of the eight frequencies, each having separate channels for the in-phase and out-of-phase components. The eight $\Delta\varepsilon^*_{sensor^k}$ data points are stored in the 16 coefficients $A_i$ such that $$\Delta\varepsilon^*_{sensorK} = A_{(2K-1)} + jA_{2K}.$$

The effect that the presence of a particle has on the effective permittivity of fluid within the sensor can be described by dielectric mixture theory.
From this mixture theory, $$\varepsilon^*_{sensorfluidwithparticle} = \varepsilon^*_{fluid} \frac{\left(\frac{v_{sensor}}{v_{particle}}\right) + 2\left(\frac{\varepsilon^*_{particle} - \varepsilon^*_{fluid}}{\varepsilon^*_{particle} + 2\varepsilon^*_{fluid}}\right)}{\left(\frac{v_{sensor}}{v_{particle}}\right) - \left(\frac{\varepsilon^*_{particle} - \varepsilon^*_{fluid}}{\varepsilon^*_{particle} + 2\varepsilon^*_{fluid}}\right)},$$

giving the sensor signal, which arises from the difference in the fluid properties in the left and right sections of the sensor, as:

$$\Delta\varepsilon^*_{sensor} = \varepsilon^*_{fluid} \left( \frac{\left(\frac{\varepsilon^*_{particle} - \varepsilon^*_{fluid}}{\varepsilon^*_{particle} + 2\varepsilon^*_{fluid}}\right)}{\left(\frac{v_{sensor}}{v_{particle}}\right) - \left(\frac{\varepsilon^*_{particle} - \varepsilon^*_{fluid}}{\varepsilon^*_{particle} + 2\varepsilon^*_{fluid}}\right)} \right).$$

In each expression, all complex permittivities (denoted by the stars) take the form $\varepsilon^* = \varepsilon - j\sigma/\omega$ as before.

As already indicated the particle usually has a very small volume compared to the sensor so that $$\left(\frac{v_{sensor}}{v_{particle}}\right)$$

is very large. Therefore, the signal expression can usually be accurately approximated as:

$$\Delta\varepsilon^*_{sensor} = \varepsilon^*_{fluid} \left(\frac{v_{particle}}{v_{sensor}}\right)\left(\frac{\varepsilon^*_{particle} - \varepsilon^*_{fluid}}{\varepsilon^*_{particle} + 2\varepsilon^*_{fluid}}\right).$$

The permittivity and conductivity of the suspending fluid and the sensor volume are known for a given measurement condition, leaving the particle volume and complex permittivity as the only unknowns. The goal of analyzing the impedance signals further is to deduce these parameters. The coefficients $A_i$ representing the values $\Delta\varepsilon^*_{sensor^k}$ for eight measurement frequencies may be subjected to further filtering to lower the effect of noise of the measurements. Dielectric theory requires that both the real and imaginary components of $\Delta\varepsilon^*_{sensor}$ be continuous functions of frequency and that the real (in phase component) $\Delta\varepsilon_{sensor}$ either remains constant with increasing frequency or else decreases with increasing frequency. The rate of change of these functions with frequency are also limited because the narrowest dielectric response in a dispersive system is that given by the Debye dispersion function, which has a width at half height of about 1.1 decades of frequency. Lastly, the Kramers-Kronig relationship also requires that the real and imaginary parts of $\Delta\varepsilon^*_{sensor}$ obey the relationship:

$$\Delta\varepsilon_{sensor}(f) = a + \int_f^0 (\Delta\sigma_{sensor} - \Delta\sigma_0) \cdot \partial \ln(f),$$

where $\alpha$ is a constant and $\Delta\sigma_0$ is related to the DC conductivity of the particle. For the geometrically-spaced measurements frequencies f, 2f, 4f, ... used in one embodiment, this means that the coefficients $A_{(2k-1)}$ must be related to the coefficients $A_k$ by $$A_{2K-1} = a_0 + A_1 + a_g \sum_1^K (A_{2k} - A_2) \text{ for } K > 1,$$

where $\alpha_o$ and $\alpha_g$ are offset and gain parameters relating to the electronics and algorithms earlier in the signal processing sequence that are constant for a given event. In one embodiment, the coefficients $A_i$ may be analyzed by a curve fitting procedure and replaced by best-fit values that obey all of these constraints. This has the effect of lowering measurement noise.

If a dielectric model exists for the particles under investigation, then that model may also be used to deduce explicit characteristics of the particles from the massaged $A_i$ coefficients. For example, the dielectric properties of mammalian cells can be modeled to a good approximation by a single shell structure. This structure comprises an electrically homogeneous cell cytoplasm of radius r having complex permittivity $\varepsilon^*_{int}$ surrounded by a thin membrane of thickness d and permittivity $\varepsilon^*_{mem}$. The complex permittivity of such a particle is given by:

$$\varepsilon^*_{particle} = \varepsilon^*_{mem} \frac{\left(\frac{r+d}{r}\right)^3 + 2\left(\frac{\varepsilon^*_{int} - \varepsilon^*_{mem}}{\varepsilon^*_{int} + 2\varepsilon^*_{mem}}\right)}{\left(\frac{r+d}{r}\right)^3 - \left(\frac{\varepsilon^*_{int} - \varepsilon^*_{mem}}{\varepsilon^*_{int} + 2\varepsilon^*_{mem}}\right)}.$$

As before, each complex permittivity takes the form $\varepsilon^* = \varepsilon - j\sigma/\omega$, and $\varepsilon^*_{mem}$ reflects the cell membrane permittivity and conductivity and $\varepsilon^*_{int}$ reflects the cell interior permittivity and conductivity. Because the complex permittivity of a particle described by this model is highly frequency dependent, it is possible to use an iterative fitting algorithm to fit the particle permittivity equation to the coefficients $A_i$ to yield best-fit estimates for the cell volume, the cell cytoplasmic conductivity and permittivity, and the cell membrane conductivity and permittivity. As is known in the art, other dielectric models may be used for specific particle types as appropriate and the above analysis adjusted accordingly.

In one embodiment, the DSP uploads the massaged coefficients $A_i$ for each particle event to a host personal computer. This computer uses a Nelder-Meade simplex algorithm or other non-linear curve fitting procedure to derive values for $v_{particle}$, $\epsilon_{mem}$, and $\sigma_{int}$ for each particle, and displays the accumulated results for all particle events during an experiment on dot plots and histograms in a fashion similar to that commonly employed for displaying flow cytometry data. The host computer also allows communications with the DSP and FPGA systems to set the measurement and data analysis parameters for those systems.

As already indicated, the single shell model fairly closely approximates the dielectric characteristics of mammalian cells. In order to most effectively measure the explicit cell parameters, it is helpful to undertake impedance measurements under conditions where the cell permittivity is a strong function of frequency so that the fitting of coefficients $A_i$ by the dielectric shell model may be robust. For the frequency range of measurements in the present embodiment, this occurs when the conductivity of the cell suspending fluid is much lower than the conductivity of viable cells. Typical cytoplasmic conductivity values for viable cells are ~0.6 S/m, so that conductivities for the suspending fluid of 0.1 S/m or lower are preferred. Under these conditions, the difference between the permittivity of viable cells and that of their suspending medium changes from a negative value to a positive value as frequency is increased and is zero at a so-called crossover frequency. Ideally, the suspending fluid conductivity has a value chosen to causes the crossover frequency of the modal cell type in the experimental sample to be close to 8f, the center frequency probed in the 8-frequency, octave spaced embodiment.

When necrotic cells are suspended in the low conductivity suspending fluid, they typically lose ions from their interiors causing their cytoplasmic conductivity to fall. Such damaged cells do not exhibit a crossover frequency and may be easily distinguished by impedance measurements from healthy cells of the same type that have retained their cytoplasmic ions. In this way impedance sensor measurements may be used to discriminate viable cells from non-viable and necrotic cells. This provides a useful tool for assessing cell viability in tissue culture facilities, for example.

The membrane permittivity of cells has also been shown to be highly characteristic of cell type and to changes for a given cell type during cell division, apoptosis, and if cells are exposed to biological signals, are chemically modified, or are damaged by toxins. For these reasons, different cell types may be discriminated and identified by the AC impedance sensing method. In addition, changes in cell physiology and morphology and cell responses to various agents may be deduced from impedance sensor data. Other data analysis steps appropriate to different particle measurement applications may be accomplished by appropriate adjustment of the analysis procedure.

Impedance Measurement Steps

Figure 33:
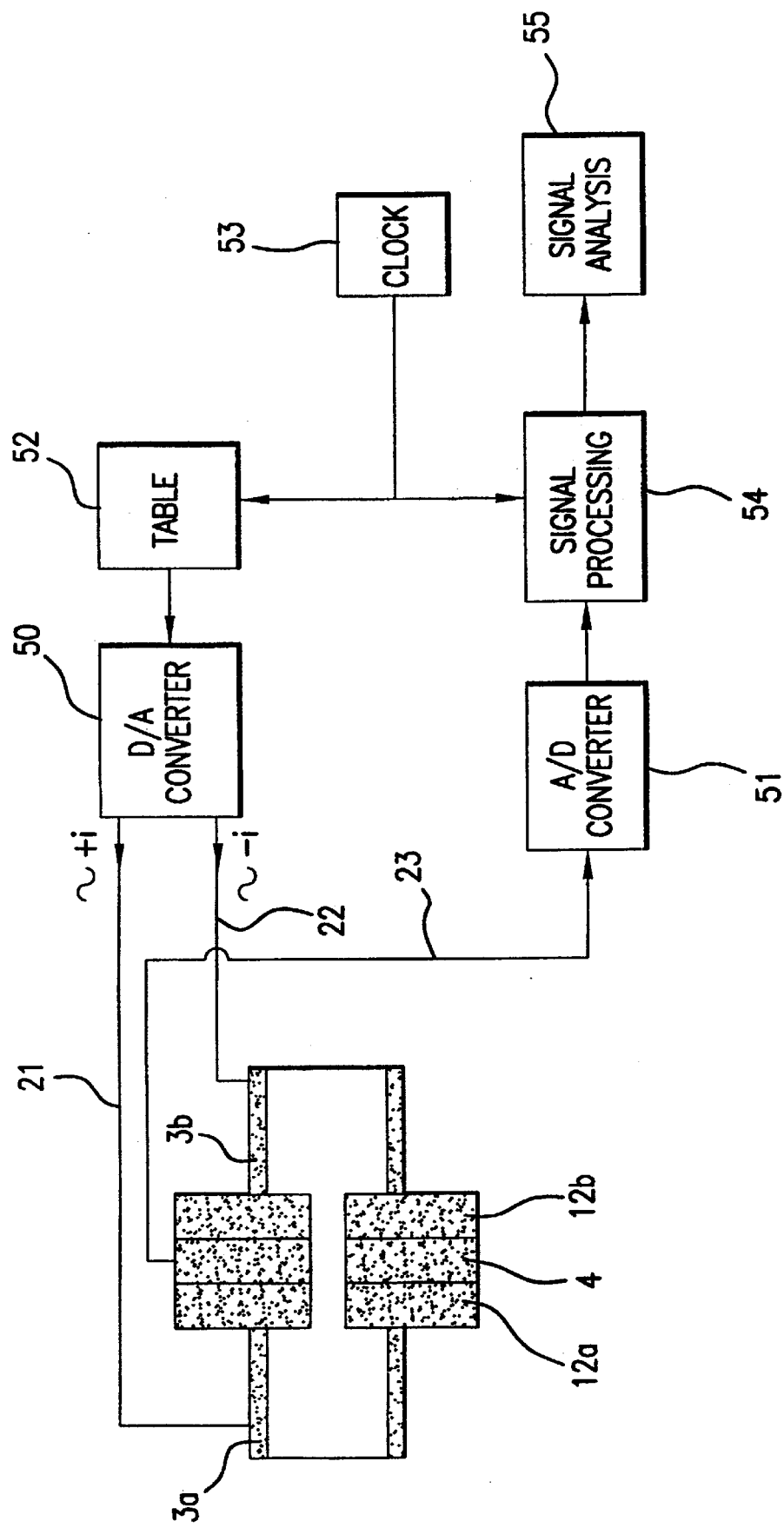
FIG. 33 is a combination flowchart and schematic diagram that illustrates impedance measurement steps, according to embodiments of the present disclosure.

FIG. 33 displays a summary of impedance measurement steps, according to embodiments of the present disclosure. Flow of suspending medium brought about by a pressure differential across the sensor channel drives the sample and the suspended particles through the sensor. The boxes represent functionality embodied in the support electronics. It is assumed that the excitation signals 21 and 22 are generated digitally from a lookup table containing waveforms of composite sine frequencies ($f_1, f_2, f_3 \ldots f_n$) 52 before going through a digital to analog converter 50. It is also assumed that the sensor signal 23 is analyzed digitally after going through an analog to digital converter 51, although analog methods may be used for either or both processes as is known in the art. A clock signal 53 may be used to synchronize the excitation and analysis process. After obtaining the sensor signal 23, the signal is sent to a signal processing 54, where the sensor signal 23 is multiplied by each one of the sine frequencies ($f_1, f_2, f_3 \ldots f_n$) and subjected to low pass filtering in n separate parallel processes to yield a continuous stream of sensor data for each frequency (1–n). Perturbations in the sensor data that follow the characteristic reversal of peaks are recognized as particle responses, and sets of impedance data at the different frequencies are output for each particle. Signal analysis 55 of the sensor signal 23 involves analyzing the sets of impedance data corresponding to particles and correcting the data for trajectory, based upon transit time through the sensor channel 11. A frequency spectrum for each particle may be constructed and used for particle identification or classification. The fluid flow rate and flow profile may be computed and used to calculate the particle concentration.

Concentration Algorithm

As stated previously, embodiments of the present disclosure may be used to analyze the concentration of samples. This specific, non-limiting embodiment may involve the following general steps:
1. Measure signal intensity and transit time for multiple (e.g., about 500) particles. Record time for entire measurement.
2. (Optional) Construct frequency histogram for transmit times (using, e.g., data such as that from FIG. 19).
3. (Optional) Curve fit histogram to laminar (or other type) flow profile.
4. Find mean time and divide it into a factor to convert it to flow rate through the orifice.
5. Calculate total volume by multiplying flow rate by time for entire measurement.
6. Calculate particle concentration by dividing number of particles counted by volume of entire measurement.

Those having skill in the art will recognize, with the benefit of this disclosure, that several other methods may be utilized to use the techniques explored herein to calculate properties such as concentration. All such modifications are deemed to be within the scope of this disclosure.

Different Cell Models

As is known in the art, different cell types possess characteristically different dielectric properties. In addition, inert particles such as dusts and smokes possess strikingly different dielectric frequency spectra from biological cells. Dielectric differences between different particles can be detected by techniques of the present disclosure, and this allows particles in homogeneous suspensions to be identified and dissimilar particles in heterogeneous particulate mixtures to be profiled according to their dielectric differences. In this way, blood cell differential analysis may be accomplished by impedance sensing, and cells such as bacterial spores may be discriminated from other cell types such as mammalian cells and pollen and from inert particles.

Therefore, the techniques of the present disclosures are suitable for use as a detection and discrimination element for use not only in clinical applications involving cell suspensions and in other applications where particle profiling is desirable, but also in biological agent applications in agriculture, aquaculture, and warfare and terrorism detection applications. The impedance technology may be used in a stand-alone form or as an in-line detection element for other devices. For example, the technology may be used in conjunction with devices and methods such as those disclosed in U.S. Pat. Nos. 6,287,832; 5,993,632; 5,993,630; 5,888,370; and 5,858,192 (each of which is incorporated by reference) in order to provide particle detection and discrimination capabilities. In addition, the techniques of this disclosure may be used to discriminate between different subpopulations of beads or other particles chosen so as to possess characteristic dielectric differences including dielectrically-engineered packets. In this regard, U.S. patent application Ser. No. 09/883,112, which is hereby incorporated by reference, may be useful.

Electrode Design

The driving electrodes and sensor electrodes may be formed using any method known in the art. They may be formed in conjunction with the capillary or reaction surface or coupled after forming both elements. In one embodiment, the electrodes may be formed by laminating the materials.

FIGS. 34A and 34B show a design of an impedance sensor according to embodiments of the present disclosure in which the driver 3 and sensor 4 electrodes are microfabricated inside a fluidic channel 11 of circular cross section within a dielectric body 10. The fluid flow profile is analogous to that present in the laminated membrane design, and the signal shapes and signal processing methods for deducing the fluid flow characteristics and the particle impedance corrections are the same. This microfabricated embodiment may be realized for fluidic channels consisting of capillary tubes as well as for fluidic channels within larger structures. One constraint on the material in which the impedance sensor is constructed is that it should be of low conductivity relative to the carrier medium in which particles to be sensed are carried through the channel. In the design shown, the channel has circular cross section, and the electrodes circle the channel, as represented by the dotted line around the channel shown in the end view.

An alternative design of the impedance sensor (FIGS. 35A and 35B) is one in which the driver 3 and sensor 4 electrodes are microfabricated inside a fluidic channel 11 of rectangular cross section. In one embodiment, the electrodes may be fabricated on two opposing sides of the channel case. The fluid flow profile is analogous to, but more complex, than that present in flow channels of circular cross section, and the signal shapes and signal processing methods for deducing fluid flow characteristics and particle impedance corrections are correspondingly different from the circular sensor channel cases but handled in an analogous manner as will be understood by those of ordinary skill in the art. This microfabricated embodiment may be realized for fluidic channels in capillary tubes or in larger structures where rectangular channels may be easier to realize. The material in which the impedance sensor is constructed should be of low conductivity relative to the carrier medium in which particles to be sensed are carried through the channel.

The electrodes may be formed using standard photolithography techniques. For example, one may refer to, e.g., D. Qin et al., "Microfabrication, Microstructures and Microsystems," Microsystem Technology in Chemistry and Life Sciences (Ed. Manz and Becker), Springer, Berlin, 1997, pp 1–20, which is incorporated herein by reference. Also, one may refer to Madou, Fundamentals of Microfabrication, CRC Press, Boca Raton, 1997, which is incorporated herein by reference. Depending upon the particular application, and the nature of the packets and partitioning medium, the size and spacing of electrodes may be smaller than, of similar size, or larger than the diameters of the packets. The spacing between the driving electrodes and sensor electrodes may vary, but in one embodiment, the spacing may be between about 2 microns and about 50 $\mu$m. The electrodes may have different forms such as lines, squares, circles, diamonds, polygons, or other suitable shapes. The dimensions of each electrode may vary, but a typical electrode may be between about 0.2 $\mu$m and about 10 mm., and more particularly, between about 1 $\mu$m and about 200 $\mu$m.

Definitions

As used herein, a "carrier fluid" refers to matter that may be adapted to suspend other matter to form packets on a reaction surface. A carrier fluid may act by utilizing differences in hydrophobicity between a fluid and a packet. For instance, hydrocarbon molecules may serve as a carrier fluid for packets of aqueous solution because molecules of an aqueous solution introduced into a suspending hydrocarbon fluid will strongly tend to stay associated with one another. This phenomenon is referred to as a hydrophobic effect, and it allows for compartmentalization and easy transport of packets. A carrier fluid may also be a dielectric carrier liquid which is immiscible with sample solutions. Other suitable carrier fluid include, but are not limited to, air, aqueous solutions, organic solvents, oils, and hydrocarbons.

As used herein, a "programmable fluid processor" (PFP) refers to an electrode array whose individual elements can be addressed with different electrical signals. The addressing of electrode elements with electrical signals may initiate different field distributions and generate dielectrophoretic or other manipulation forces that trap, repel, transport, or perform other manipulations upon packets on and above the electrode plane. By programmably addressing electrode elements within the array with electrical signals, electric field distributions and manipulation forces acting upon packets may be programmable so that packets may be manipulated along arbitrarily chosen or predetermined paths. The impedance sensor may also be coupled to an integrated circuit which is coupled to the PFP. The impedance sensor may also be coupled to a controller which is coupled to the PFP. The controller may be adapted to provide a feedback from the impedance sensor to the PFP.

Counter phase, or anti-phase means that the two electrodes are driven by identical but opposite currents. The identical but opposite current signals (+i) and (−i) must be within 5% or more preferably 2% of the ideal values.

As used herein, "packet" and "particle" both refer to any compartmentalized matter. The terms may refer to a fluid packet or particle, an encapsulated packet or particle, and/or a solid packet or particle. A fluid packet or particle refers to one or more packets or particles of liquids or gases. A fluid packet or particle may refer to a droplet or bubble of a liquid or gas. A fluid packet or particle may refer to a droplet of water, a droplet of reagent, a droplet of solvent, a droplet of solution, a droplet of sample, a particle or cell suspension, a droplet of an intermediate product, a droplet of a final reaction product, or a droplet of any material. An example of a fluid packet or particle is a droplet of aqueous solution suspended in oil. The packet or particle may be encapsulated or a solid. Examples of solid packets or particles are a latex microsphere with reagent bound to its surface suspended in an aqueous solution, a cell, a spore, a granule of starch, dust, sediment and others. Methods for producing or obtaining packets or particle as defined herein are known in the art. Packets or particles may vary greatly in size and shape, as is known in the art.

As used herein, an "array" refers to any grouping or arrangement. An array may be a linear arrangement of elements. It may also be a two dimensional grouping having columns and rows. Columns and rows need not be uniformly spaced or orthogonal. An array may also be any three dimensional arrangement.

All of the methods disclosed and claimed herein can be made and executed without undue experimentation in light of the present disclosure. While the techniques of this invention have been described in terms of specific embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A impedance sensor comprising:
   a sensor electrode;
   first and second driver electrodes coupled to the sensor electrode and driven in counter phase to produce a net output signal of about zero at the sensor electrode; and
   a fluid channel defined through the sensor electrode and the first and second driver electrodes.

2. The impedance sensor of claim 1, wherein the sensor electrode comprises copper.

3. The impedance sensor of claim 1, wherein the sensor electrode comprises a first and second dielectric membrane sandwiching a detector electrode.

4. The impedance sensor of claim 3, wherein the first or second dielectric membrane comprises polyimide.

5. The impedance sensor of claim 3, wherein the first or second dielectric membrane is laminated.

6. The impedance sensor of claim 3, wherein the first and second driver electrodes contact the first and second dielectric membranes, respectively.

7. The impedance sensor of claim 1, wherein the first and second driver electrodes are driven at multiple frequencies.

8. The impedance sensor of claim 1, wherein the first and second driver electrodes are driven with an alternating current signal.

9. The impedance sensor of claim 1, wherein the cross section of the channel is rectangular.

10. The impedance sensor of claim 1, further comprising a programmable fluid processor coupled to the sensor electrode.

11. A flow-through impedance sensor, comprising:
    a fluid channel for transporting a carrier medium and particles through the impedance sensor;
    a composite membrane sensor assembly coupled to the channel and comprising a detector electrode sandwiched between first and second dielectric membranes;
    first and second driver electrodes coupled to the channel and positioned adjacent opposite sides of the composite membrane sensor assembly, the first and second driver electrodes being driven in counter phase to produce:
    (a) a net output signal of about zero at the detector electrode when no particle is within the impedance sensor; and
    (b) a non-zero net output signal at the detector electrode when a particle is within the impedance sensor.

12. The impedance sensor of claim 11, wherein the first and second driver electrodes are in contact with the composite membrane sensor assembly.

13. The impedance sensor of claim 11, wherein the first and second driver electrodes are driven at multiple frequencies.

14. The impedance sensor of claim 11, wherein the first and second driver electrodes are driven with an alternating current signal.

15. The impedance sensor of claim 11, further comprising a programmable fluid processor coupled to the sensor electrode.

16. A method for determining a characteristic of a packet, comprising:
    flowing a fluid containing a packet through an impedance sensor that includes first and second driver electrodes driven in counter phase to produce a net output signal of about zero at a sensor electrode;
    measuring perturbations of the net output signal arising from changes in impedance associated with the presence of the packet within the impedance sensor; and
    determining the characteristic of the packet from the perturbations.

17. The method of claim 16, wherein the characteristic of the packet comprises packet size.

18. The method of claim 16, wherein the characteristic of the packet comprises packet transit time through the impedance sensor.

19. The method of claim 16, wherein the characteristic of the packet comprises packet velocity.

20. The method of claim 16, wherein the characteristic of the packet comprises packet concentration.

21. The method of claim 16, wherein the characteristic of the packet comprises a relative displacement within the impedance sensor.

22. The method of claim 16, wherein the characteristic of the packet comprises packet impedance.

23. A method for determining a characteristic of a particle, comprising:
    providing an impedance sensor comprising a sensor electrode, first and second driver electrodes coupled to the sensor electrode and driven in counter phase to produce a net output signal of about zero at the sensor electrode, and a channel defined through the sensor electrode and the first and second driver electrodes;
    applying a multi-frequency drive signal to the first and second driver electrodes;
    receiving an impedance signal from the sensor electrode;
    determining in-phase and out-of-phase components of the impedance signal at the frequencies of the drive signal;
    detecting changes in the in-phase and out-of-phase components indicative of a particle event; and
    analyzing portions of the impedance signal about the particle event to determine the characteristic of the particle.

24. The method of claim 23, wherein the drive signal comprises a composite of separate waveforms of different frequencies, each frequency being an integer multiple of a fundamental frequency.

25. The method of claim 24, wherein the drive signal consists of 8 separate sine waves having frequencies f, 2f 4f 8f, 16f, 32f 64f and 128f.

26. The method of claim 23, wherein impedance signal components are represented as 24 bit words.

27. The method of claim 23, further comprising deriving a composite signal comprising a moving sum of magnitudes of changes of the in-phase and out-of-phase components.

28. The method of claim 27, wherein detecting changes indicative of a particle event comprises determining when the composite signal exceeds a threshold value above a noise floor.

29. The method of claim 23, wherein analyzing portions of the impedance signal about the particle event to determine the characteristic of the particle comprises calculating an overlap integral.

30. The method of claim 23, wherein analyzing portions of the impedance signal about the particle event to determine the characteristic of the particle comprises constraining curves associated with the in-phase and out-of-phase components to obey a Kramers-Kronig relationship.

31. The method of claim 23, wherein analyzing portions of the impedance signal about the particle event to determine the characteristic of the particle comprises determining a velocity of the particle.

32. The method of claim 23, wherein analyzing portions of the impedance signal about the particle event to determine the characteristic of the particle comprises determining a mean fluid velocity.

33. The method of claim 23, wherein analyzing portions of the impedance signal about the particle event to determine the characteristic of the particle comprises determining a concentration of particles.

34. The method of claim 23, wherein analyzing portions of the impedance signal about the particle event to determine the characteristic of the particle comprises determining a size of the particle.

35. The method of claim 23, wherein analyzing portions of the impedance signal about the particle event to determine the characteristic of the particle comprises determining a relative displacement of the particle.

36. The method of claim 23, wherein analyzing portions of the impedance signal about the particle event to determine the characteristic of the particle comprises determining a dielectric property of the particle.

37. The method of claim 23, wherein analyzing portions of the impedance signal about the particle event to determine the characteristic of the particle comprises determining a conductivity property of the particle.

38. The method of claim 23, wherein analyzing portions of the impedance signal about the particle event to determine the characteristic of the particle comprises determining an impedance of the particle.

39. The method of claim 23, wherein analyzing portions of the impedance signal about the particle event to determine the characteristic of the particle comprises determining a cell membrane permittivity of the particle.

40. The method of claim 23, wherein analyzing portions of the impedance signal about the particle event to determine the characteristic of the particle comprises determining a cytoplasmic permittivity of the particle.

* * * * *

UNITED STATES PATENT AND TRADEMARK OFFICE
CERTIFICATE OF CORRECTION

PATENT NO. : 6,703,819 B2
DATED : March 9, 2004
INVENTOR(S) : Gascoyne et al.

It is certified that error appears in the above-identified patent and that said Letters Patent is hereby corrected as shown below:

Column 26,
Lines 61-62, delete "2f 4f 8f" and insert -- 2f, 4f, 8f --.
Line 62, delete "32f 64f" and insert -- 32f, 64f, --.

Signed and Sealed this

Tenth Day of August, 2004

JON W. DUDAS
*Acting Director of the United States Patent and Trademark Office*